(12) United States Patent  (10) Patent No.:  US 6,347,938 B1
Ma  (45) Date of Patent:  Feb. 19, 2002

(54) ORTHODONTIC CUTTERS

(76) Inventor: Joon Ma, 303ho Pyunghwa Plaza, 1054-5 IL-san 3 dong, IL San-Gu, 411-313 (KR)

( * ) Notice: Subject to any disclaimer, the term of this patent is extended or adjusted under 35 U.S.C. 154(b) by 0 days.

(21) Appl. No.: 09/675,161

(22) Filed: Sep. 29, 2000

(30) Foreign Application Priority Data

Jun. 10, 2000 (KR) .......................................... 00-31909

(51) Int. Cl.[7] .............................................. A61C 7/02
(52) U.S. Cl. ...................................................... 433/4
(58) Field of Search ............................... 433/4, 3, 144, 433/148, 157, 159; 140/118, 121

(56) References Cited

U.S. PATENT DOCUMENTS 4,392,494 A * 7/1983 Ashby ........................ 128/326
5,542,843 A * 8/1996 Price ............................. 433/4

FOREIGN PATENT DOCUMENTS

DE  3738950 A1 * 5/1989

\* cited by examiner

*Primary Examiner*—Gene Mancene
*Assistant Examiner*—Melba Bumgarner
(74) *Attorney, Agent, or Firm*—Burns, Doane, Swecker & Mathis, L.L.P.

(57) ABSTRACT

An orthodontic cutter, which comprises a cutter part 1 including a pair of handles 11, one of the handles being shorter than the other, which cross at a pivot axis and a pair of jaws 13 which have cutting edges; a tucker part 2 including a short stick-type handle 21 having the lower end thereof provided with a tip 211; a holder 12 formed on the lower lateral side of the shorter one of the handles 11 of the cutter part 1 and provided with an insertion hole 121; an insertion post 22 formed on the top end of the short stick-type handle 21 of the tucker part 2, provided with a clamping hole 221, and inserted into the insertion hole 121 of the holder 12; and a clamping bolt 3 mated with the clamping hole 221 for holding the insertion post 22 in the insertion hole 121. In the orthodontic cutter, the tucker part 2 is detachably incorporated with the cutter part 1, being able to perform a rotation movement on its own axis. This invention is allowed to perform two functions, i.e., cutting off the ends of the ligature wires at the right length and tucking the trimmed ends of the ligatures. Several embodiments of incorporation mechanism are provided.

20 Claims, 24 Drawing Sheets

Prior Art

Prior Art

Prior Art

Prior Art

ORTHODONTIC CUTTERS

This application claims priority under 35 U.S.C. §§119 and/or 365 to Kr2000-31909 filed in Korea on Jun. 10, 2000; the entire content of which is hereby incorporated by reference.

BACKGROUND OF THE INVENTION

1. Technical Field of the Invention

The present invention generally relates to an orthodontic cutter and, more particularly, to a plier-type orthodontic cutter detachably incorporated with a stick-type ligature tucker for the increased efficiency and convenience in using instruments necessary to the art of orthodontic dentistry.

2. Background Art

In a conventional procedure of orthodontic treatment, as illustrated in FIG. 1, a bracket 30 having a slot 20 is bonded to a target tooth 10 of an orthodontic patient and then held in interconnection with other brackets by an arch wire 40 inserted into the individual slots 20. For stabilizing the arch wire 40 seated in the bracket slots 20, a ligature wire "L" is tied to the wings of each bracket 30, i.e., the ligature wire "L" is placed over the arch wire 40 and around the wings of the bracket 30 and then, the ends of the ligature wire "L" are knotted together by making use of a ligation instrument 50 lest the arch wire 40 should get loose from the bracket slots 20.

But, the unnecessary excess end of the knotted ligature wire should be cut off and, in addition, the sharp end of the cutaway ligature wire should be tucked inwardly to protect the lips, cheeks and gums of the patient. So, an orthodontic cutter 60 and a ligature tucker 70 are normally used to cut off the excess end of the ligature wire "L" in a short length and to direct the sharp end of the cutaway ligature wire toward the underside of the arch wire 40.

The conventional orthodontic cutter 60 and ligature tucker 70 which have been most popularly used in the orthodontic treatment are essentially distinct in configuration from each other, as illustrated in FIGS. 2 and 3, respectively. Referring to FIG. 2, the orthodontic cutter 60 has a pair of handles 61 which cross at a pivot axis in symmetrical configuration and a pair of jaws 62 which are provided with cutting edges. Referring to FIG. 3, the ligature tucker 70 has a stick-type handle 71 whose lower end is integrally provided with a tip 72, the tip 72 being straight, narrow and thin, and notched. While the tip 72 is usually straight, an angled tip is often employed according to the dentist's preference.

However, the orthodontic cutter and the ligature tucker are essentially distinct in configuration from each other and of no co-operative relationship, so that the dentist has to alternately use the cutter and the tucker in a troublesome way for engaging the arch wire with the brackets bonded to all the teeth of the orthodontic patient, i.e., iteratively cutting and bending the ends of the ligature wire tied to the individual brackets. If the dentist should proceed to cut off the excess ends of the ligature wires at another side of the patient's dentition without tucking the sharp ends of the ligature wires which have been already cut at one side to avoid the alternate uses of the cutter and the tucker, the sharp and untucked ends of the ligature wires would hurt the soft tissues of the orthodontic patient. The above-described drawbacks of the separate orthodontic cutter and the separate ligature tucker, which must be used in an alternate manner with much inexpedience, result in extreme deterioration of working efficiency in the orthodontic treatment, i.e., making the dentist have a difficulty in concentrating his or her attention and extending the working time in treating the orthodontic patient.

SUMMARY OF THE INVENTION

Accordingly, the present invention is contrived to solve the problems pertaining to the orthodontic cutter and the ligature tucker conventionally used as orthodontic instruments.

It is the principal object of the present invention to provide a novel orthodontic cutter detachably incorporated with a ligature tucker, in which the orthodontic cutter and the ligature tucker essentially distinct in configuration from each other and of no co-operative relationship are combined into a single incorporated structure, which makes it possible to overcome the disadvantages of alternately using the separate instruments without saying that it can successfully fulfill the respective inherent functions of the cutter and the tucker in the incorporated state, thus enhancing the working efficiency in handling the orthodontic instruments.

It is another object of the present invention to provide a novel orthodontic cutter detachably incorporated with a ligature tucker, allowing the user to optionally disassemble the cutter or the tucker from the incorporated structure and to easily replace or repair the disassembled parts upon finding a breakdown, wherein the tucker is optionally replaceable with any other similar orthodontic hand instrument distinct in configuration of the tip but able to perform the function of the tucker, such as band seater or scaler.

To achieve the above objects of the present invention, there is provided an orthodontic cutter, which will be described in detail by referring to FIGS. 4 and 5 as one of the several preferred embodiments. The orthodontic cutter comprises a cutter part 1 including a pair of handles 11, one of the handles being shorter than the other, which cross at a pivot axis and a pair of jaws 13 which have cutting edges; a tucker part 2 including a short stick-type handle 21 having the lower end thereof provided with a tip 211; a holder 12 formed on the lower lateral side of the shorter one of the handles 11 of the cutter part and provided with an insertion hole 121; an insertion post 22 formed on the top end of the short stick-type handle 21 of the tucker part 2, provided with a clamping hole 221, and inserted into the insertion hole 121 of the holder 12; and a clamping bolt 3 mated with the clamping hole 221 for holding the insertion post 22 in the insertion hole 121. In the orthodontic cutter, the tucker part 2 is detachably incorporated with the cutter part 1, being able to perform a rotation movement on its own axis.

BRIEF DESCRIPTION OF DRAWIINGS

Other objects and aspects of the invention will become apparent from the following description of embodiments with reference to the accompanying drawings in which.

DESCRIPTION OF THE PREFERRED EMBODIMENT

Figure 1:
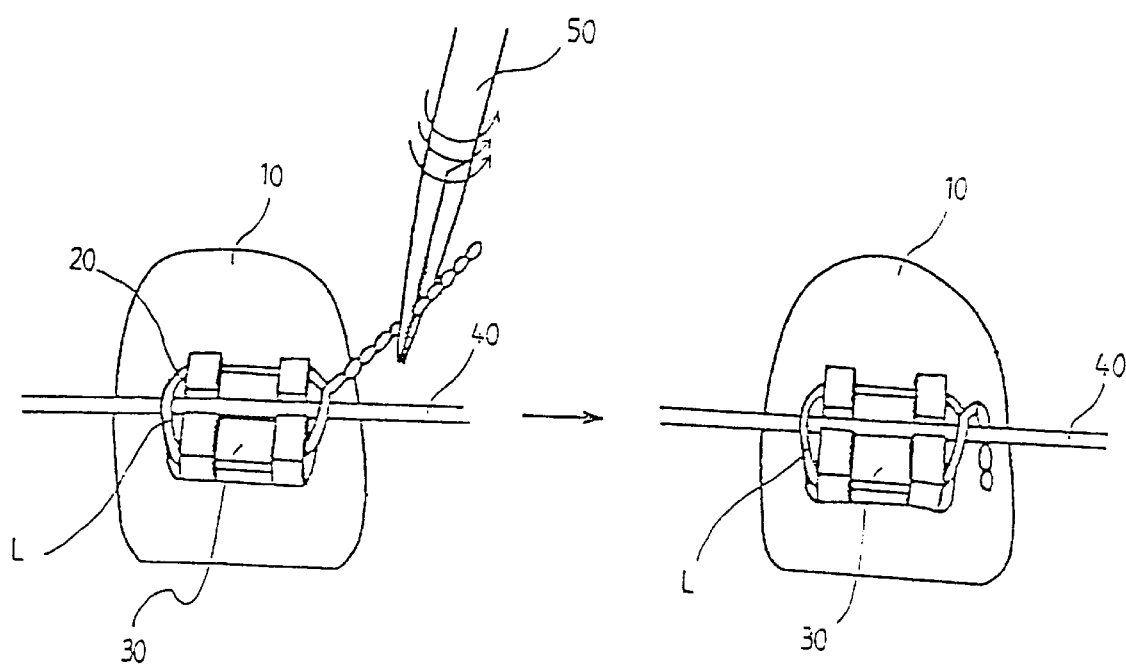
FIG. 1 is a diagram illustrating a routine procedure for ligation of an orthodontic arch wire.
Figure 2:
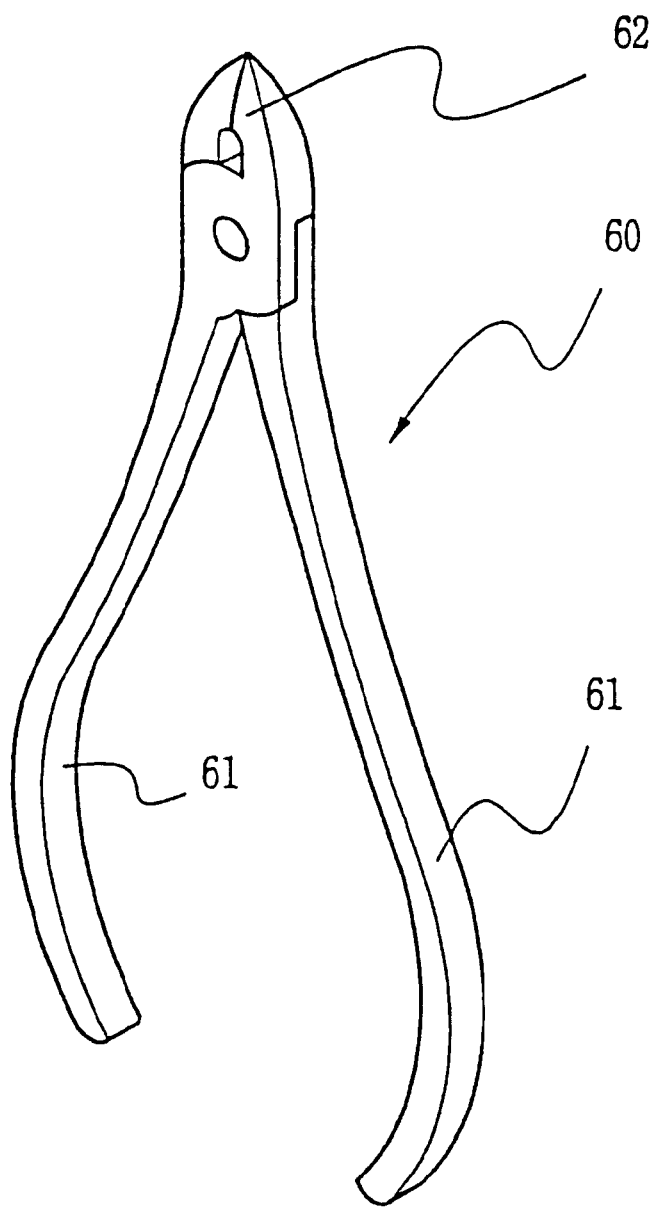
FIG. 2 is a schematic view of a conventional orthodontic cutter.
Figure 3:
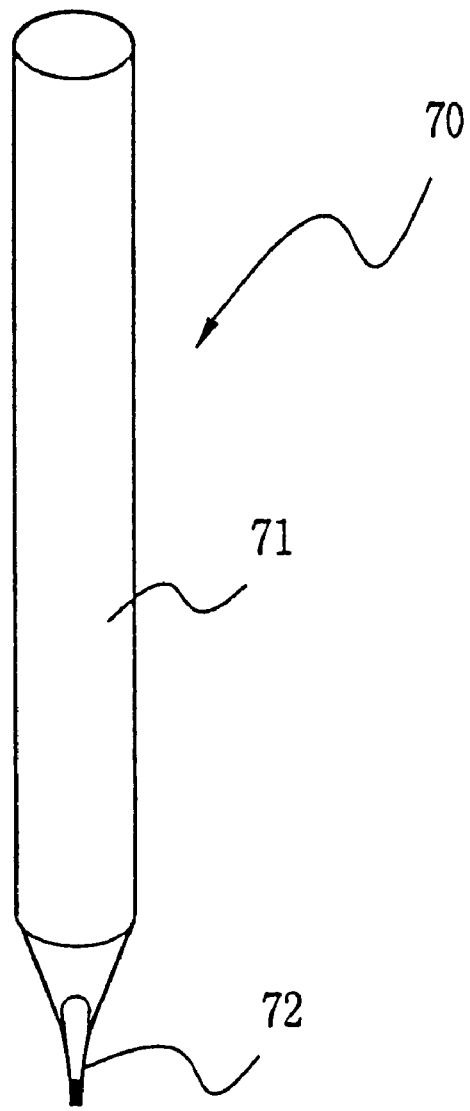
FIG. 3 is a schematic view of a conventional ligature tucker.

Preferred embodiments of the orthodontic cutter of the present invention will be described in detail with reference to the accompanying drawings. Like reference numerals denote the same components in the drawings.

Figure 4:
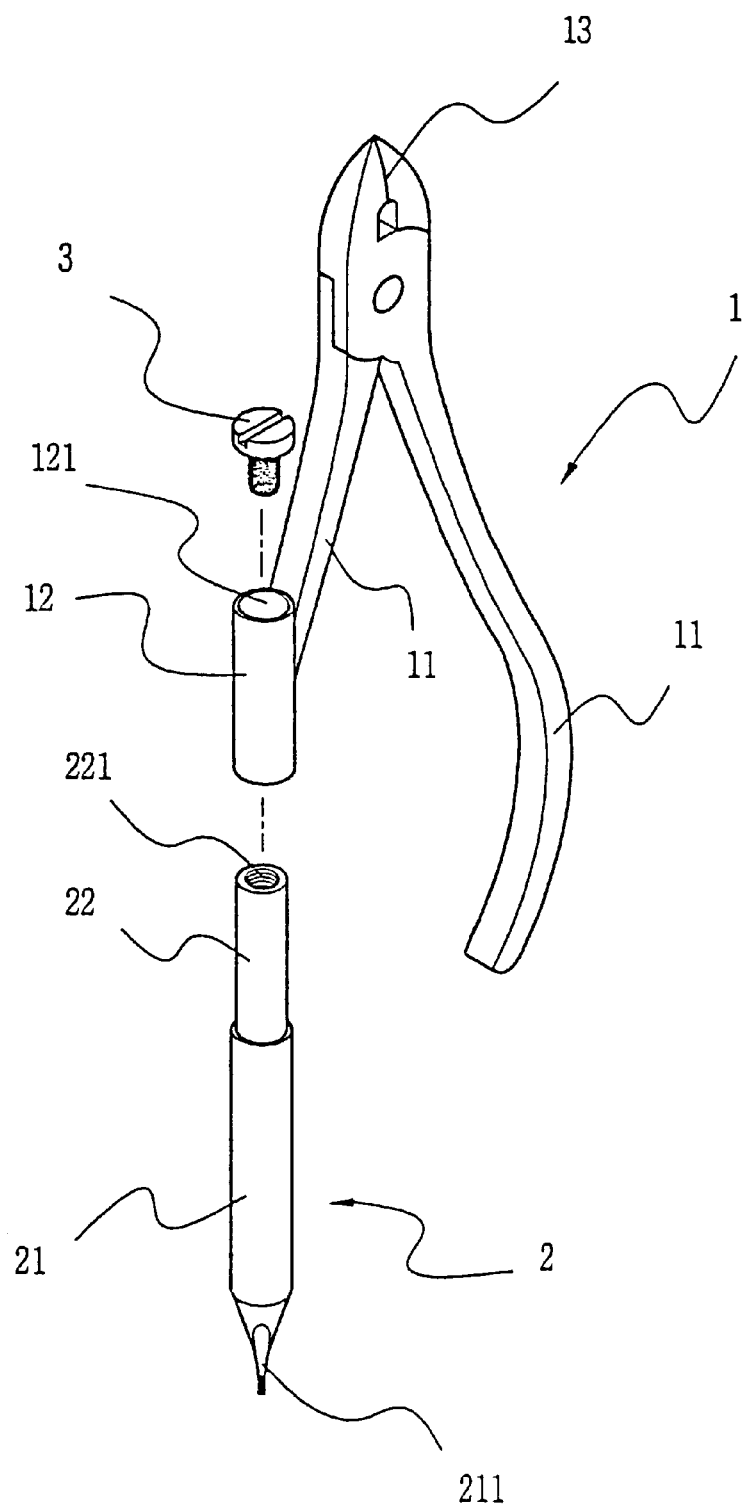
FIG. 4 is a perspective view of an orthodontic cutter in accordance with a first embodiment of the present invention.
Figure 5:
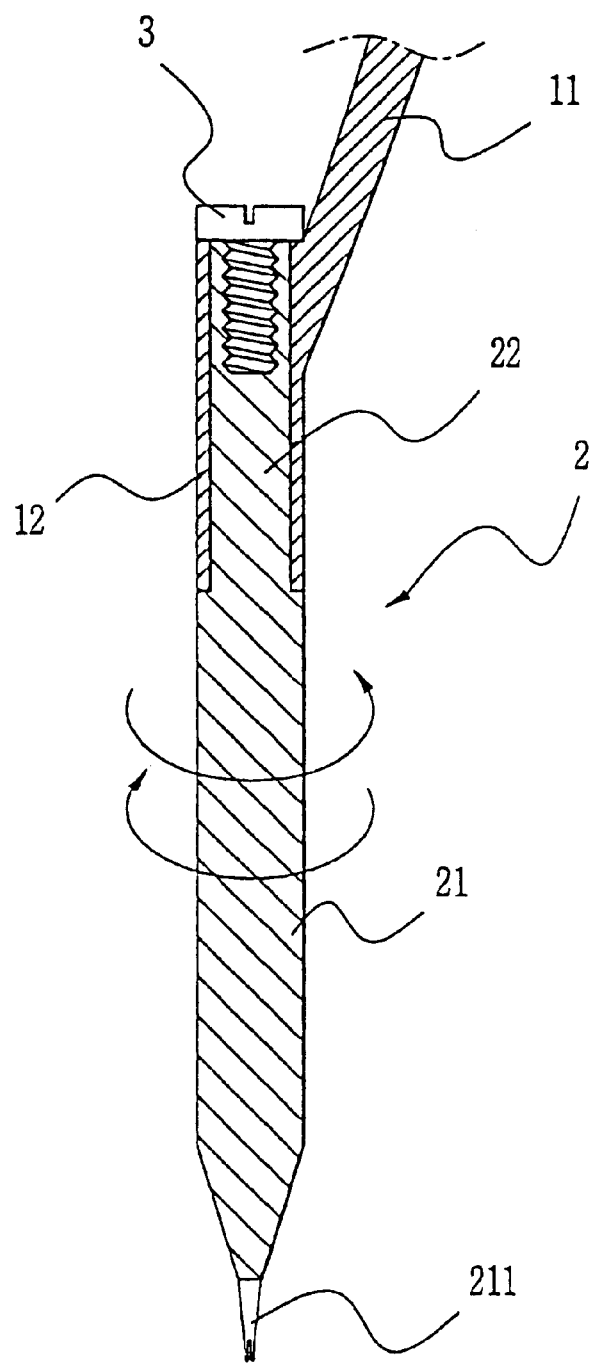
FIG. 5 is a longitudinal sectional view partially illustrating the assembled state of the ligature tucker in accordance with the first embodiment of the present invention.

FIG. 4 is an exploded perspective view showing an orthodontic cutter in accordance with a first embodiment of the present invention, and FIG. 5 is a longitudinal sectional view illustrating the assembled state of the ligature tucker indicated in FIG. 4.

Referring to FIG. 4, a cutter part 1 referred to as a cutter 1 for simplicity has a pair of handles 11 and a pair of jaws 13, either one of the handles 11 being shorter than the other, and a tucker part 2 referred to as a tucker 2 for simplicity has a short stick-type handle 21 and a tip 211. This will also be the same with the second to tenth embodiments.

The cutter 1 has a normal cutter structure, as shown in FIG. 4, composed of two opposite handles 11 which cross at a pivot axis and two opposite jaws 13 which have cutting edges. Preferably, one of the opposite handles 11 is shorter than the other by about half the original length and integrally provided with a holder 12 (to be described hereinafter) on the lower lateral side thereof.

The holder 12 has an essentially cylindrical structure centrally provided with an insertion hole 121 inside and runs parallel to the long axis of the cutter 1 itself, as shown in FIG. 4.

The tucker 2 has a normal tucker structure, as shown in FIG. 4, with a short stick-type handle 21 integrally provided with a tip 211 on the lower end thereof, the tip 211 being straight, narrow and thin, and notched. Preferably, the stick-type handle 21 is short as about the same length as the difference in length between the normal and shorter handles 11 of the cutter 1 and has the upper end thereof integrally provided with an insertion post 22 (to be described hereinafter).

The insertion post 22 is smaller in diameter than the stick-type handle 21, as shown in FIG. 4, and has the upper end thereof centrally provided with a clamping hole 221 having an internal thread in a desired depth. The clamping hole 221 is for mating with a clamping bolt 3.

The clamping bolt 3 has a normal connecting structure comprising a bolt head and a screw thread.

Accordingly, when the cutter 1 and the tucker 2 are assembled together, the insertion post 22 of the tucker 2 is inserted into the insertion hole 121, as shown in FIG. 4, and then the clamping bolt 3 is screwed into the clamping hole 221 of the insertion post 22, as shown in FIG. 5, thus detachably incorporating the cutter 1 with the tucker 2.

The insertion post 22 has the diameter slightly less than the inner diameter of the insertion hole 121 and hence a loose contact with the insertion hole 121, therefore the loose contact imparts circumstances for a rotation movement on its own axis to the insertion post 22 engaged in the insertion hole 121 by the clamping bolt 3.

While not illustrated in the drawings, the tucker 2 can be provided with the insertion post 22 which is longer than the holder 12 in order to be capable of doing the limited up and down movement as well as the rotation movement. The added up and down movement helps the user tuck the ligature wire ends more accurately.

Figure 6:
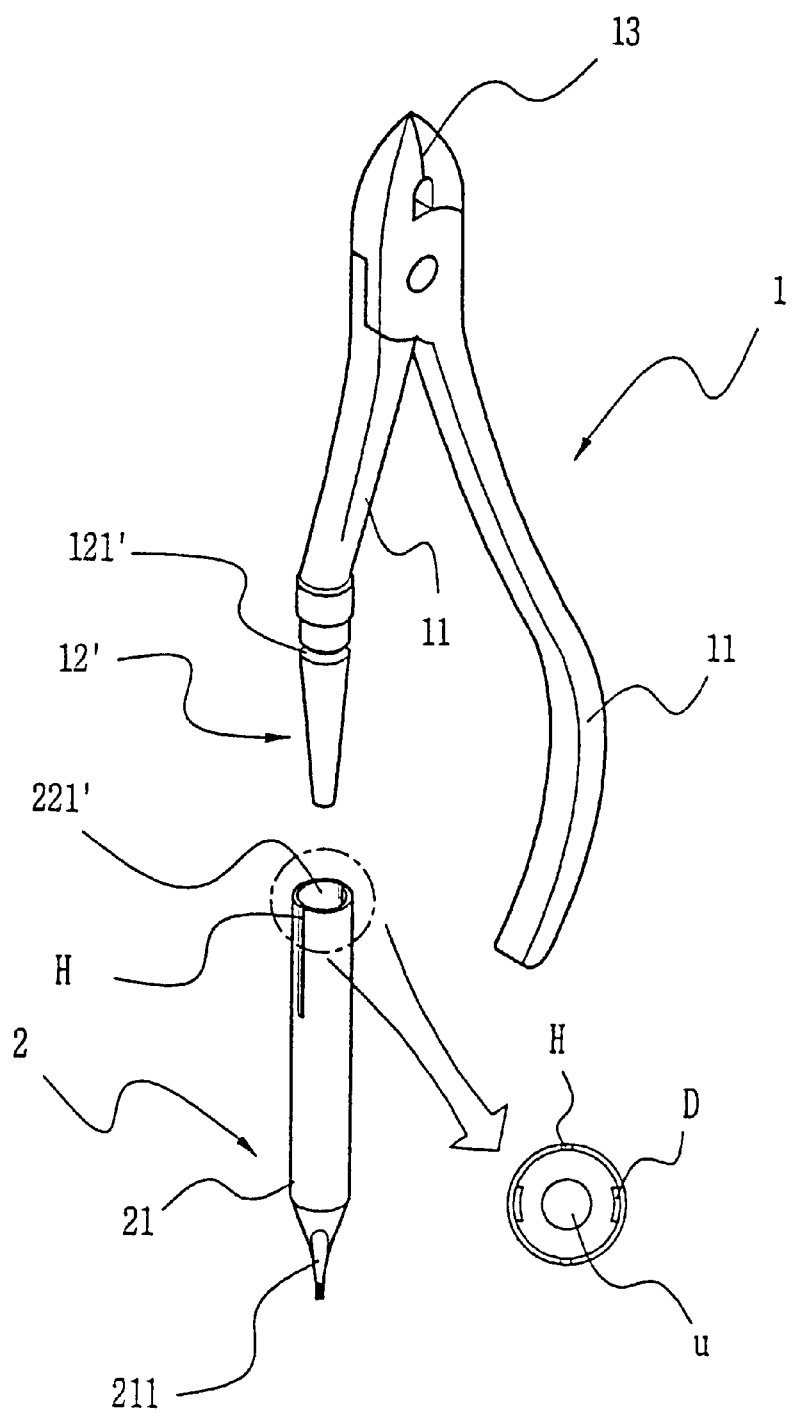
FIG. 6 is a perspective view of an orthodontic cutter and enlarged top plan view of the ligature tucker in accordance with a second embodiment of the present invention.
Figure 7:
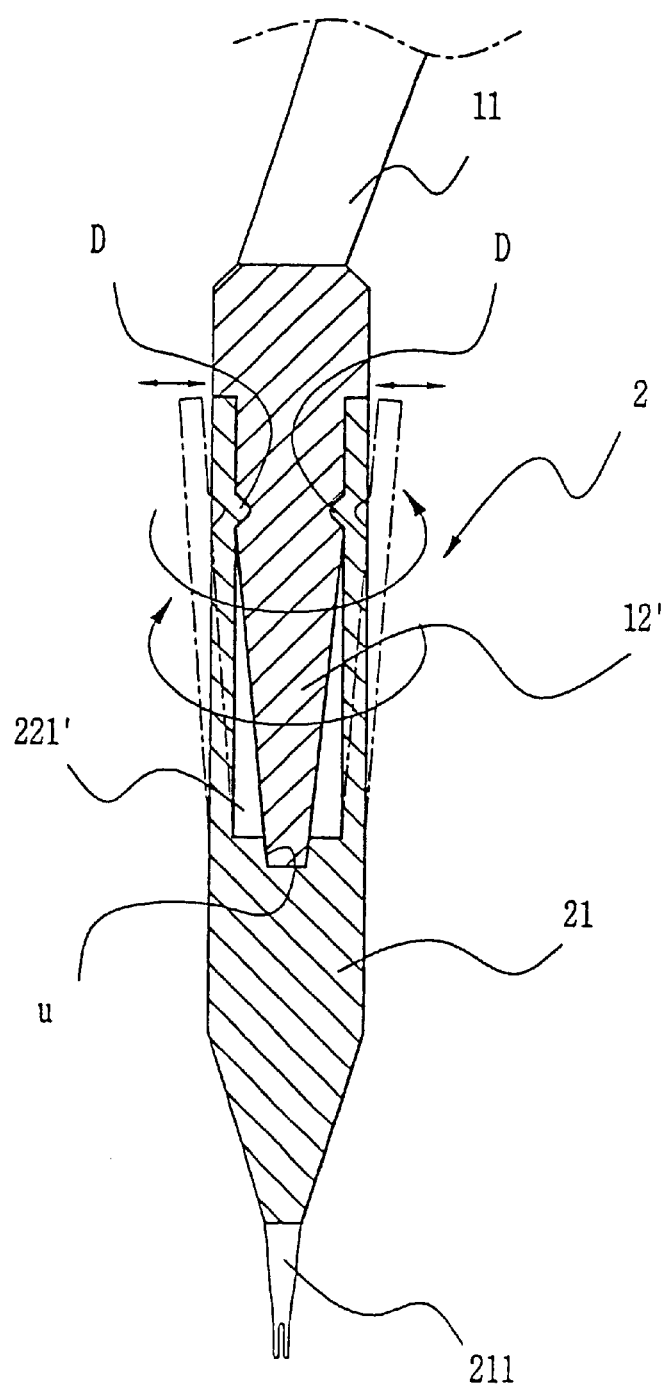
FIG. 7 is a longitudinal sectional view partially illustrating the assembled state of the ligature tucker in accordance with the second embodiment of the present invention.

FIG. 6 is an exploded perspective view of an orthodontic cutter and enlarged top plan view of a ligature tucker in accordance with a second embodiment of the present invention, and FIG. 7 is a longitudinal sectional view illustrating the assembled state of the ligature tucker indicated in FIG. 6.

Referring to FIG. 6, the orthodontic cutter of this embodiment is essentially analogous in structure to that of the first embodiment, excepting that the shorter one of the handles 11 of the cutter 1 is integrally provided with a tapered rod 12' instead of the holder 12 and that the short stick-type handle 21 of the tucker 2 has a socket 221' prepared in the upper end thereof in place of the insertion post 22.

The tapered rod 12', straightly extending from the lower end of the shorter one of the handles 11 of the cutter 1 and running parallel to the long axis of the cutter 1 itself, has a desired length enough to be completely seated into both the socket 221' and a support pit "u" which are prepared in the short handle 21 of the tucker 2, and is provided with a triangular latch groove 121' around the outer circumference of the upper portion thereof, as shown in FIGS. 6 and 7. And, as illustrated in FIG. 7, the accurate shape of the tapered rod 12' is composed of the upper non-tapered portion and the lower tapered portion whose border is the triangular latch groove 121'.

The socket 221' has a recessed hollow structure in a desired depth prepared in the upper end of the short stick-type handle 21 of the tucker 2. A pair of vertical slots "H", formed by vertically cutting down from both sides of the upper edge of the socket 221', are positioned opposite from each other for the purpose of providing the side walls of the socket 221' with the limited flexibility, as illustrated in FIG. 6. In respect to slot lengths, the vertical slots "H" should extend downward as far as the induced flexibility can permit the tapered rod 12' to be completely seated into both the socket 221' and the support pit "u". The support pit "u" having a recessed concavity structure is located in the center of the inner bottom surface of the socket 221' for supporting the lower portion of the inserted tapered rod 12', as illustrated in FIG. 7. In addition, on the inner and upper surface of the socket 221', there is integrally provided with a pair of bosses "D", positioned opposite from each other, with the shapes of curved rectangular projections in the top plan view and triangular projections in the longitudinal sectional view, which are fitted into the triangular latch groove 121', as illustrated in FIGS. 6 and 7.

Accordingly, when the cutter 1 and the tucker 2 are assembled together, the tapered rod 12 of the cutter 1 is pressed down into the socket 221' of the tucker 2, so that the vertical slots "H" permits the socket 221' to expand to the desired size for fitting the bosses "D" into the triangular latch groove 121', thereby effecting a snap-acting connection of the tapered rod 12 to the socket 221'. At the same time, the lower end of the tapered rod 12 is inserted into the support pit "u", as shown in FIG. 7, therefore the support pit "u" imparts a connection-supporting force to the tucker 2. By virtue of the above-described snap-acting mechanism, the tucker 2 is detachably incorporated with the cutter 1, being allowed to rotate on its own axis.

Figure 8:
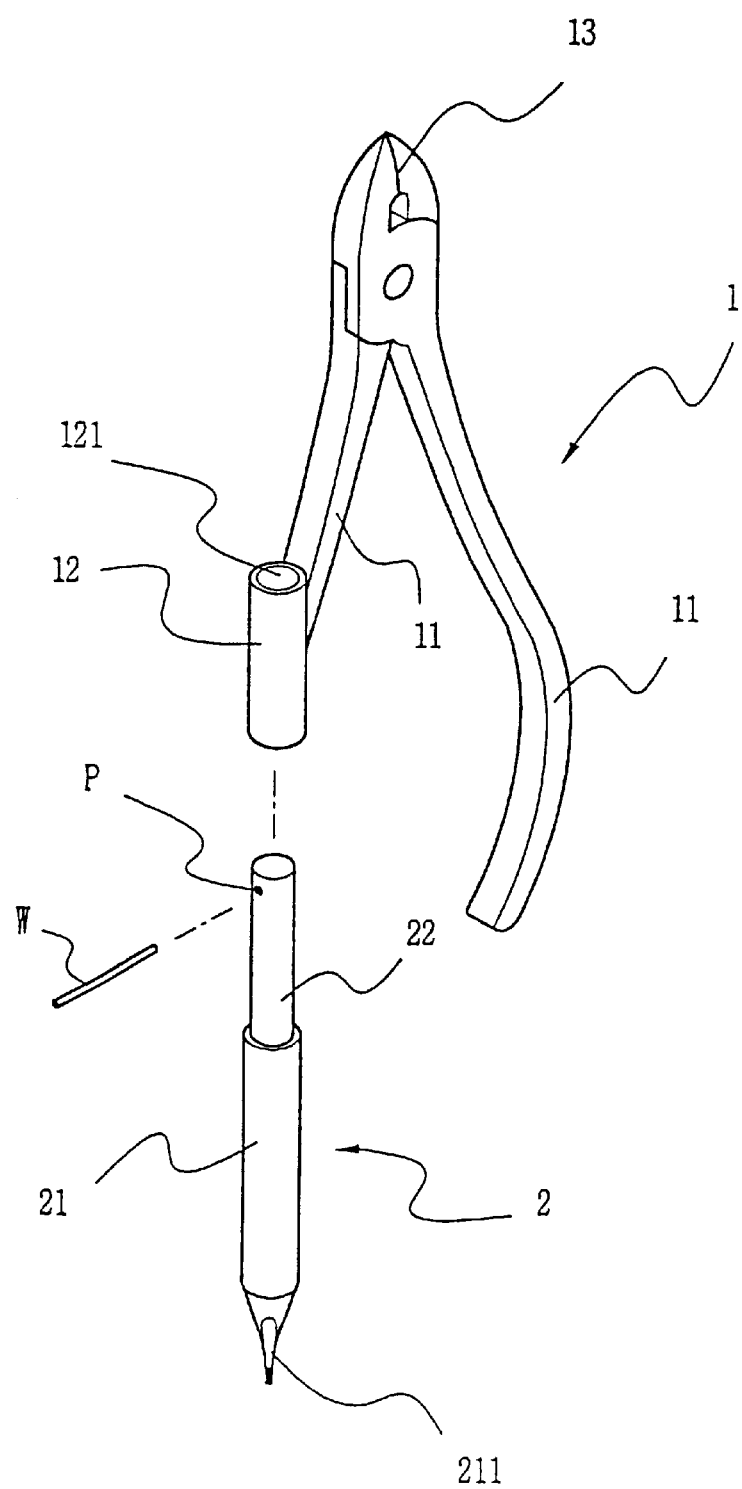
FIG. 8 is a perspective view of an orthodontic cutter in accordance with a third embodiment of the present invention.
Figure 9:
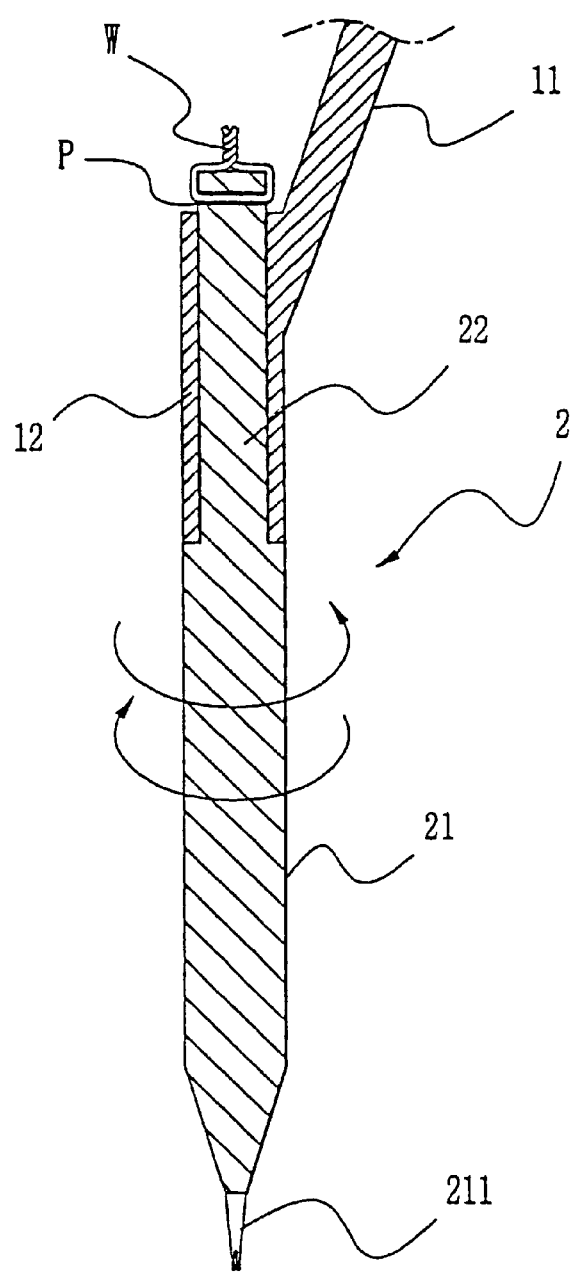
FIG. 9 is a longitudinal sectional view partially illustrating the assembled state of the ligature tucker in accordance with the third embodiment of the present invention.

FIG. 8 is an exploded perspective view of an orthodontic cutter in accordance with a third embodiment of the present invention, and FIG. 9 is a longitudinal sectional view illustrating the assembled state of the ligature tucker indicated in FIG. 8.

The orthodontic cutter of this embodiment is essentially analogous in structure to that of the first embodiment, wherein the shorter one of the handles 11 of the cutter 1 is integrally provided with the holder 12 having the insertion hole 121 and the tucker 2 has the insertion post 22 integrally formed on the top end of the short stick-type handle 21 and inserted into the insertion hole 121, excepting that the insertion post 22 is longer than the holder 12 and has a fastening hole "P", instead of the clamping hole 221, horizontally piercing the nearly top part thereof, as indicated in FIG. 8.

Accordingly, when the cutter 1 and the tucker 2 are assembled together, the insertion post 22 of the tucker 2 is inserted into the insertion hole 121 of the holder 12 to make the fastening hole "P" of the insertion post 22 exposed after having passed therethrough, as shown in FIGS. 8 and 9, and then held in the holder 12 by a separate fastening wire "W", as shown in FIG. 9. For detaching the tucker 2 from the cutter 1, the fastening wire "W" is cut away by means of another orthodontic cutter. Thus the cutter 1 is detachably incorporated with the tucker 2, allowing the tucker 2 to be rotated on its own axis.

While not shown in the drawings, the fastening hole "P" can be located at a some distance from the upper end of the holder 12 in the state of full insertion of the insertion post 22 into the insertion hole 121 of the holder 12. This adds the ability of the limited up and down movement to the tucker 2, resultantly helping the user do the tucking operation more accurately.

Figure 10:
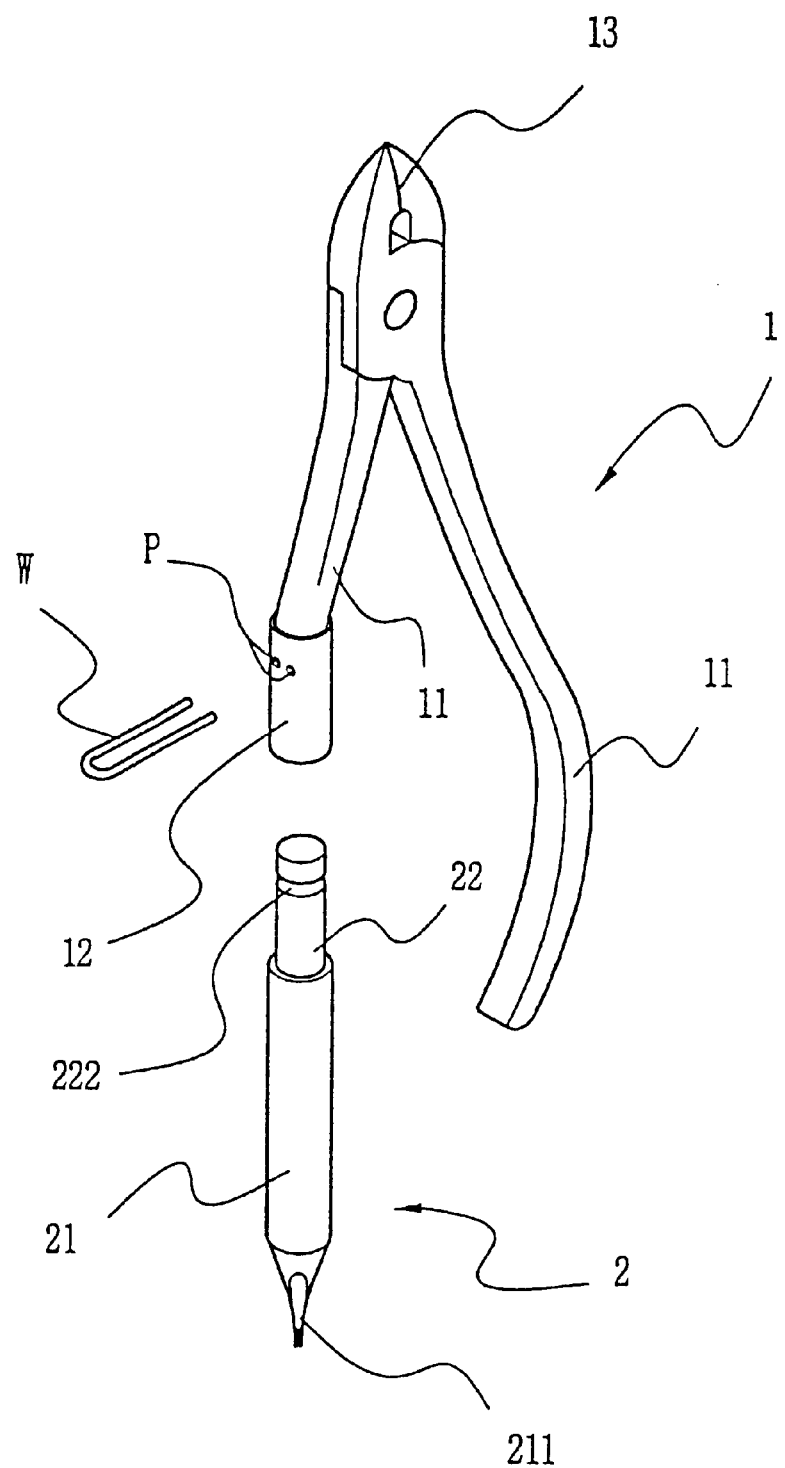
FIG. 10 is a perspective view of an orthodontic cutter in accordance with a fourth embodiment of the present invention.
Figure 11:
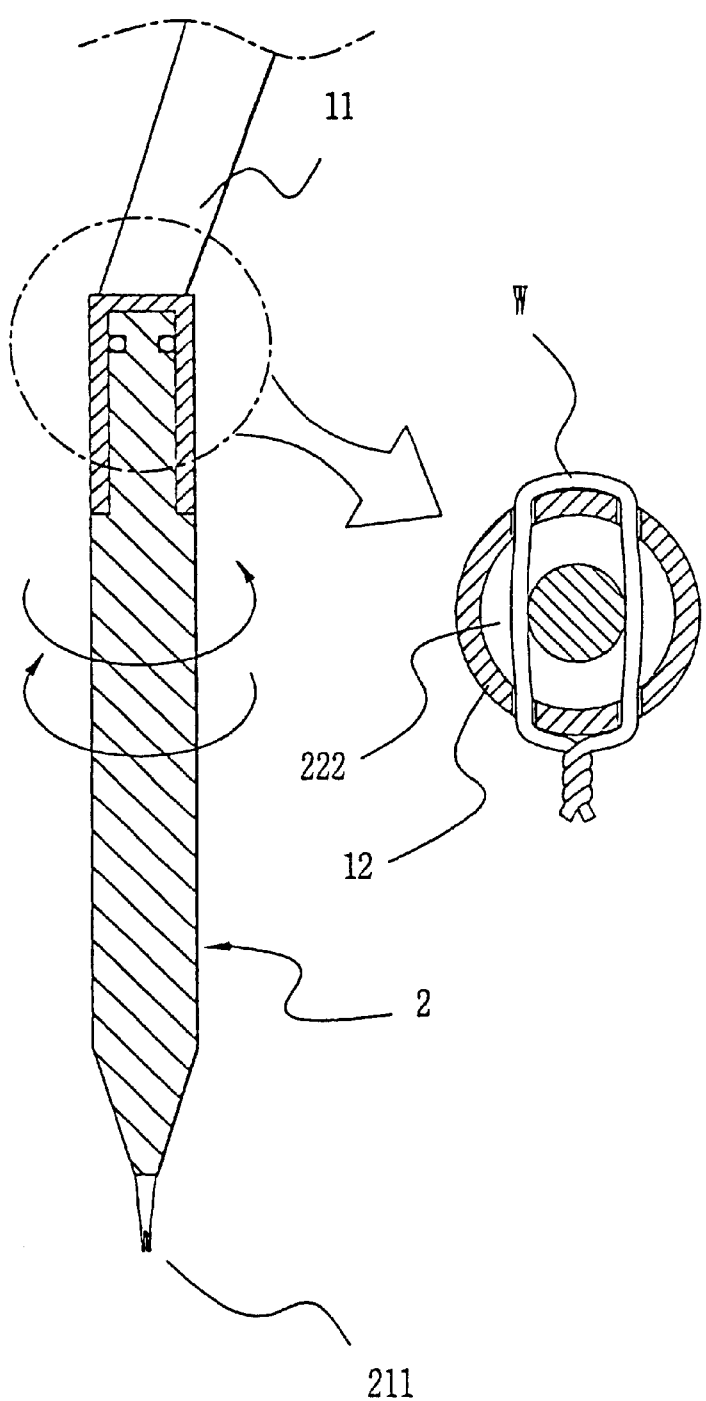
FIG. 11 is a longitudinal sectional view and enlarged cross sectional view illustrating the assembled state of the ligature tucker in accordance with the fourth embodiment of the present invention.

FIG. 10 is an exploded perspective view of an orthodontic cutter in accordance with a fourth embodiment of the present invention. FIG. 11 is a longitudinal sectional view and enlarged cross-sectional view illustrating the assemble state of the ligature tucker indicated in FIG. 10.

The orthodontic cutter of this embodiment is analogous in structure to that of the first embodiment, wherein the shorter one of the handles 11 of the cutter 1 is integrally provided with the holder 12 having the insertion hole 121 and the tucker 2 has the insertion post 22 integrally formed on the top end of the short stick-type handle 21 and inserted into the insertion hole 121, excepting that the holder 12 has the upper end thereof straightly extending from the lower end of the shorter one of the handles 11 of the cutter 1 and closed, and is provided with a pair of fastening holes "P" horizontally piercing the upper portion of the holder 12 in parallelism with each other, and that the insertion post 22 of the tucker 2 has the upper peripheral surface thereof circularly provided with a square latch groove 222, whose accurate level of location is just the same as that of the pair of fastening holes "P" in the assembled state, as shown in FIGS. 10 and 11.

Accordingly, when the cutter 1 and the tucker 2 are assembled together, the insertion post 22 of the tucker 2 is inserted into the insertion hole 121 of the cutter 1 as shown in FIG. 10, and then the insertion post 22 is secured by a separate U-shaped fastening wire "W" passing through the pair of the fastening holes "P" and the square latch groove 222 simultaneously, as shown in the partial enlarged view of FIG. 11. For detaching the tucker 2 from the cutter 1, the U-shaped fastening wire "W" is cut away by means of another orthodontic cutter. By virtue of above-described latch and latch groove-utilized incorporation mechanism, the cutter 1 is detachably incorporated with the tucker 2, allowing the tucker 2 to be rotated on its own axis.

Figure 12:
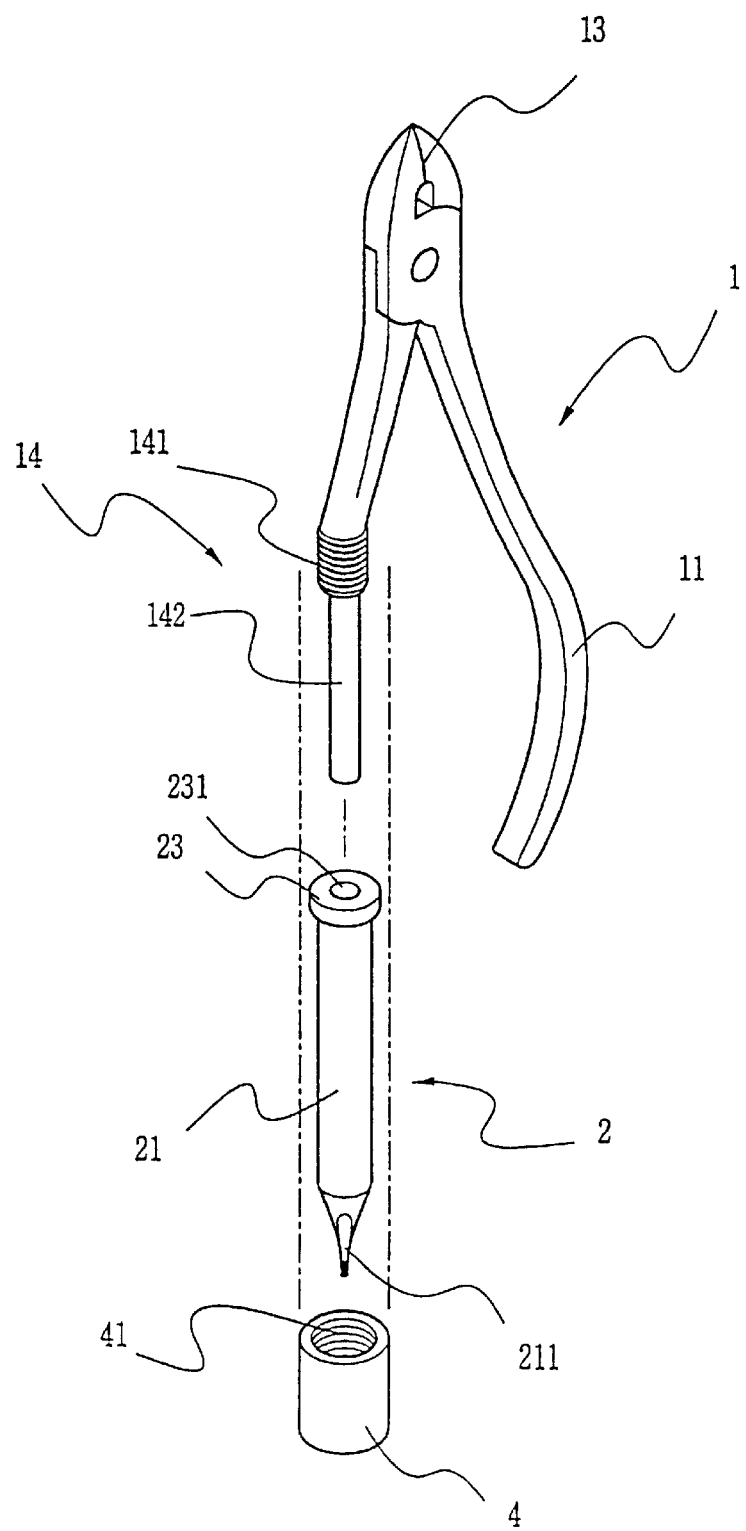
FIG. 12 is a perspective view of an orthodontic cutter in accordance with a fifth embodiment of the present invention.
Figure 13:
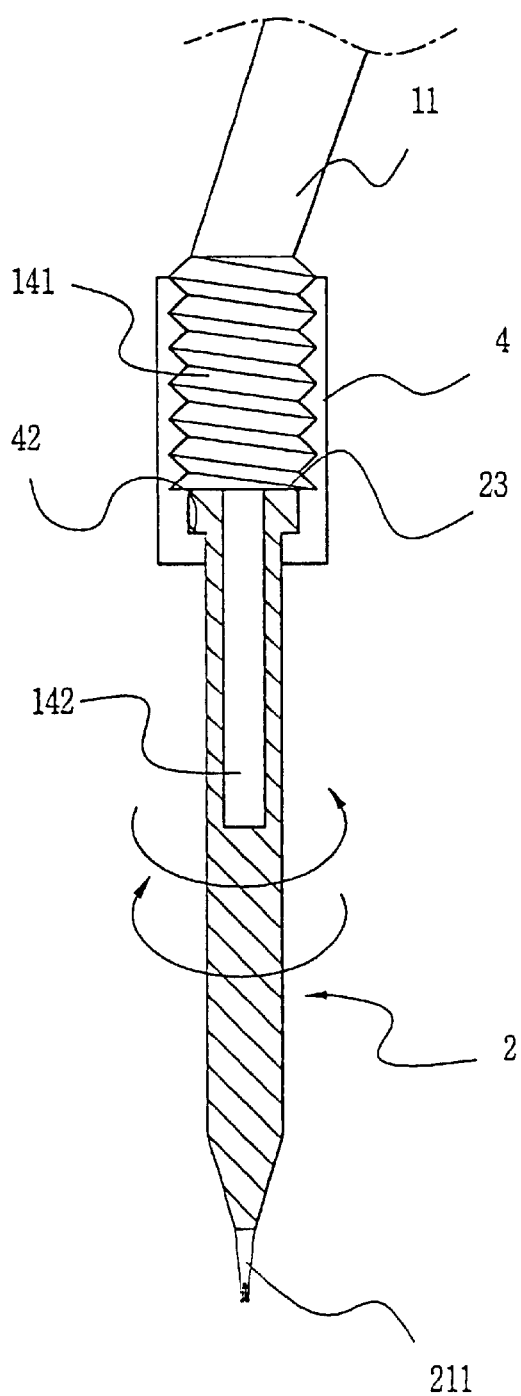
FIG. 13 is a longitudinal sectional view partially illustrating the assembled state of the ligature tucker in accordance with the fifth embodiment of the present invention.

FIG. 12 is an exploded perspective of an orthodontic cutter in accordance with a fifth embodiment of the present invention, and FIG. 13 is a longitudinal sectional view illustrating the assembled state of the ligature tucker indicated in FIG. 12.

The orthodontic cutter of this embodiment is essentially analogous in structure to that of the first embodiment, excepting that the shorter one of the handles 11 of the cutter 1 has fastening appendages 14 (to be described hereinafter), that the short stick-shaped tucker 2 has tucker appendages (to be described hereinafter) and that the incorporation of the cutter 1 with the tucker 2 is achieved by coupling the fastening appendages 14 with said tucker appendages, being secured by a coupling nut 4.

The fastening appendages 14 consist of both an external screw thread 141 integrally continuing from the lower end of the shorter one of the handles 11 of the cutter 1 and a plunger 142 integrally extending from the lower end of the external screw thread 141 with a much smaller diameter, as shown in FIG. 12. The long axes of the fastening appendages 14 are in parallelism with the long axis of the cutter 1 itself.

Said tucker appendages consist of both a flange 23 which is an annulus-shaped structure integrally formed around the periphery of the upper end of the short handle 21 of the tucker 2 and a plunger-receiving hole 23 in a desired depth in the center of the upper end of the handle 21, as shown in FIG. 12.

The coupling nut 4 is of a normal short cylinder-shaped structure having an internal thread 41 on the inner surface thereof and a nut stopper 42 at the lower end thereof.

Accordingly, when the cutter 1 and the tucker 2 are assembled together, the plunger 142 of the cutter 1 is inserted into the plunger-receiving hole 231 of the tucker 2 and then the connection is maintained by the coupling nut 4, the nut stopper 42 and the internal thread 41 of which have been passed through by the tip 221 and the handle 21 of the tucker 2 and then engaged with the flange 23 and the external screw thread 141 respectively, as shown in FIG. 13. Thus, the cutter 1 is detachably incorporated with the tucker 2.

The flange 23 secured by the coupling nut 4 has a slightly loose contact with the nut stopper 42 of the coupling nut 4, therefore the loose contact imparts circumstances for a rotation movement on its own axis to the tucker 2 attached to the cutter 1.

Figure 14:
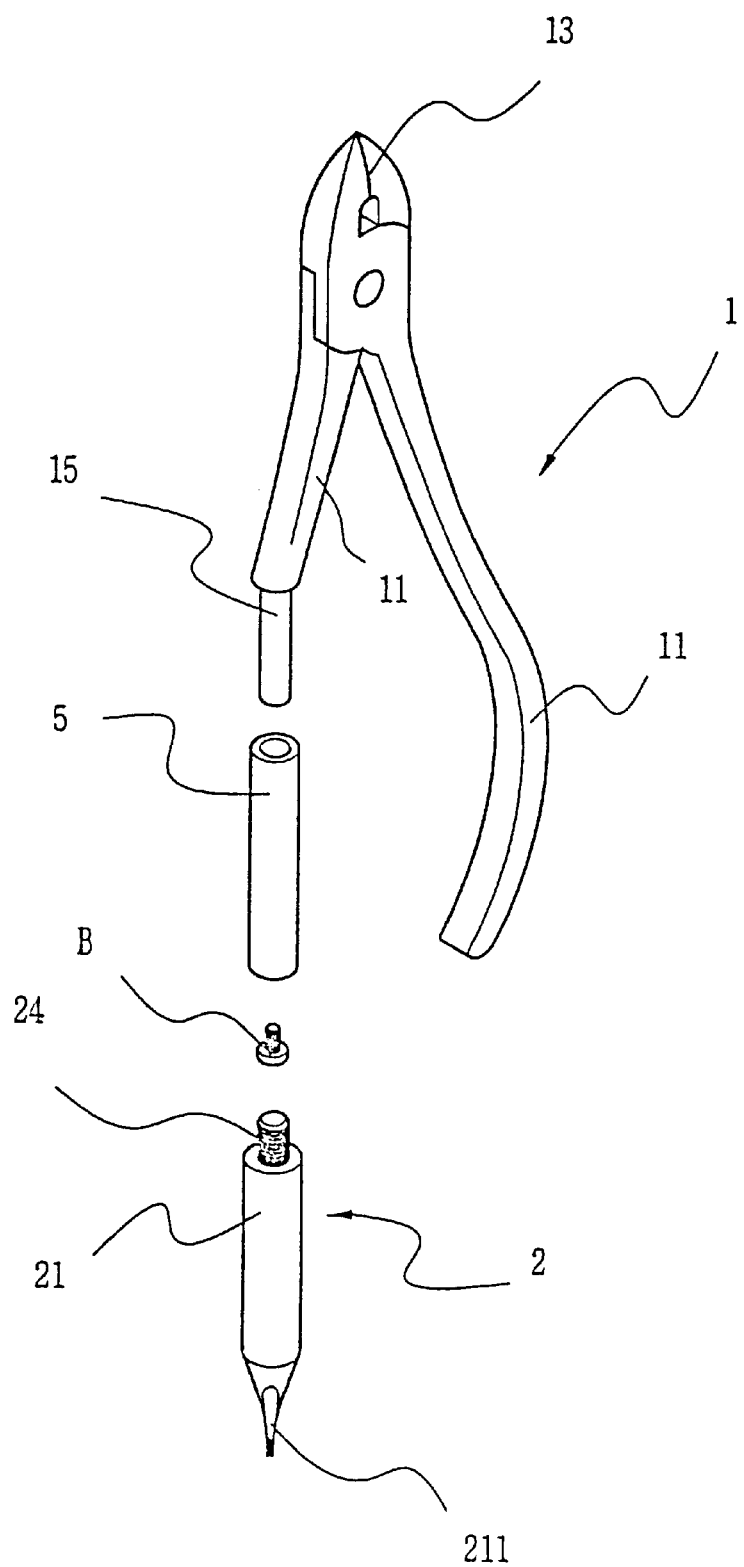
FIG. 14 is a perspective view of an orthodontic cutter in accordance with a sixth embodiment of the present invention.
Figure 15:
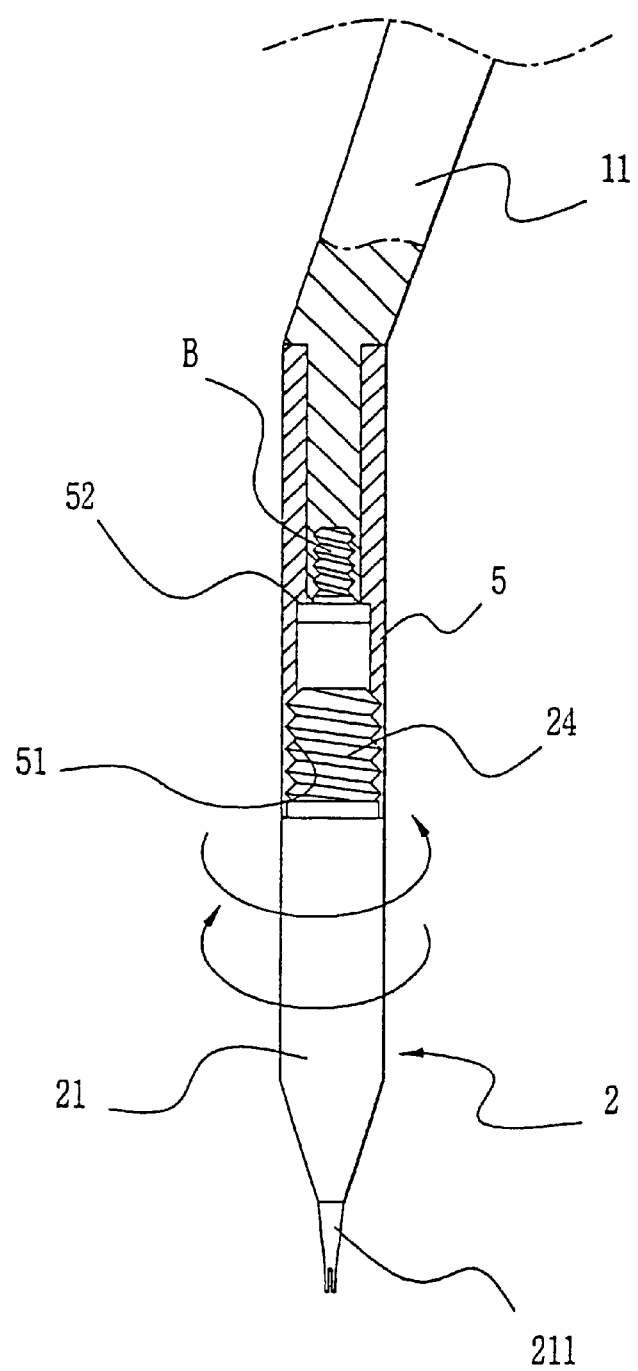
FIG. 15 is a longitudinal sectional view partially illustrating the assembled state of the ligature tucker in accordance with the sixth embodiment of the present invention.

FIG. 14 is an exploded perspective view of an orthodontic cutter in accordance with a sixth embodiment of the present invention, and FIG. 15 is a partial longitudinal sectional view illustrating the assembled state of the components shown in FIG. 14.

The orthodontic cutter of this embodiment is essentially analogous in structure to that of the first embodiment, excepting that the shorter one of the handles 11 of the cutter 1 is integrally provided with an insertion bar 15, that a separate interconnection pipe 5 is provided, and that the tucker 2 has a shorter handle 21 integrally provided with a screw post 24 on the upper end thereof.

The insertion bar 15 is, as shown in FIG. 14, an upright protrusive structure extending from the lower end of the shorter one of the handles 11 of the cutter 1 and somewhat smaller in diameter than the handle 11, and runs parallel to the long axis of the cutter 1 itself. In addition, it is provided with a screw hole in the lower end thereof for mating with a screw bolt "B".

The tucker 2 has the upper end of the shortened stick-type handle 21 centrally provided with the protrusive screw post 24 having an external thread, as shown in FIG. 14.

The interconnection pipe 5 is of a cylindrical structure in a desired length and having an internal thread 51 and a bolt stopper 52 inside, as shown in FIG. 15.

Accordingly, the assembly procedure is as follows. First, the interconnection pipe 5 is fitted onto the insertion bar 15. Second, it is held in place by screwing the screw bolt "B" up into said screw hole prepared in the lower end of the insertion bar 15 and then consequently making the head of the screw bolt "B" come into contact with the bolt stopper 52 prepared inside the interconnection pipe 5. And finally, the internal thread 51 of the interconnection pipe 5 is mated with said external thread of the screw post 24 of the tucker 2. These steps will be understood by referring to FIG. 15. Thus, the cutter 1 is detachably incorporated with the tucker 2.

The interconnection pipe 5 secured to the insertion bar 15 by the screw bolt "B" has not only an internal diameter permitting the passage of the head of the screw bolt "B", but also a slightly loose contact with the insertion bar 15, as shown in FIG. 15. The loose contact imparts circumstances for a rotation movement on its own axis to the tucker 2 as well as the interconnection pipe 5 which are firmly assembled together by means of screw joint.

Figure 16:
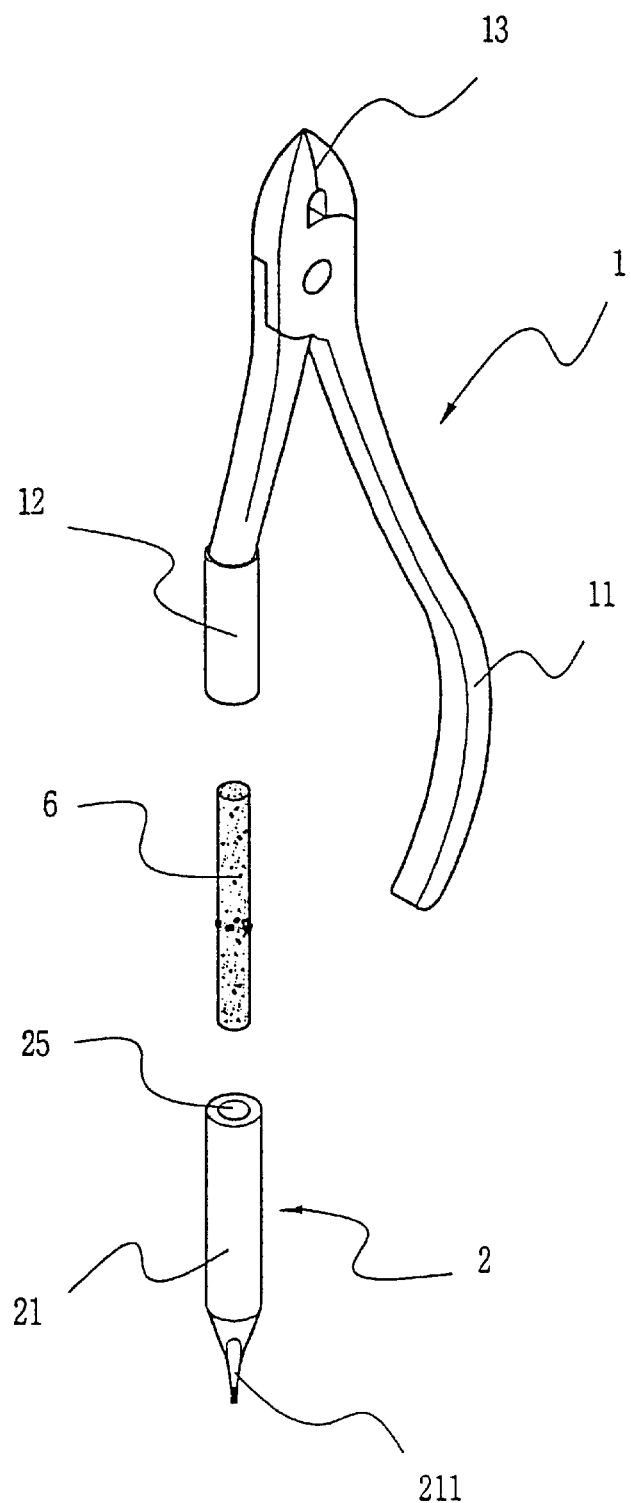
FIG. 16 is a perspective view of an orthodontic cutter in accordance with a seventh embodiment of the present invention.
Figure 17:
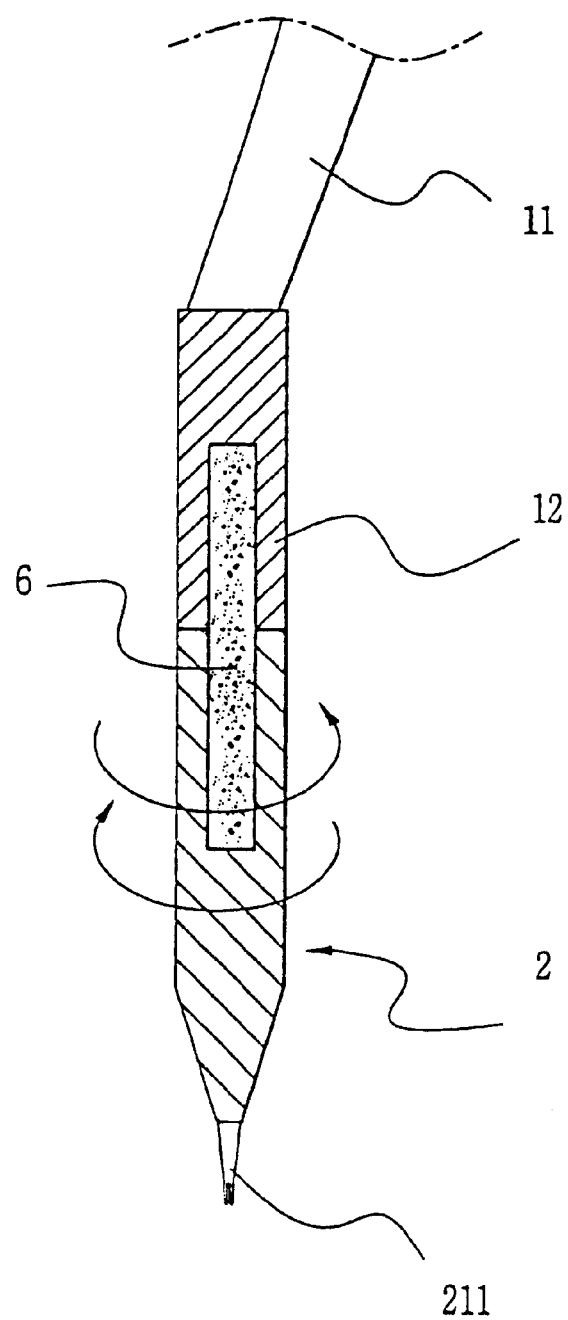
FIG. 17 is a longitudinal sectional view partially illustrating the assembled state of the ligature tucker in accordance with the seventh embodiment of the present invention.

FIG. 16 is an exploded perspective view of an orthodontic cutter in accordance with a seventh embodiment of the present invention, and FIG. 17 is a longitudinal sectional view illustrating the assembled state of the ligature tucker indicated in FIG. 16.

The orthodontic cutter of this embodiment is essentially analogous in structure to that of the first embodiment, excepting that the holder 12 has the upper end thereof straightly extending from the lower end of the shorter one of the handles 11 of the cutter 1 and closed, as shown in FIG. 17, and that the tucker 2 has the upper end of the short stick-type handle 21 centrally provided with a magnet stick-receiving hole 25 having a recessed hollow structure in a desired depth.

Accordingly, the assembly procedure is as follows. One end of a magnet stick 6 is inserted into the insertion hole 121 of the holder 12 and then the other end is inserted into the magnet stick-receiving hole 25 of the tucker 2, as shown in FIGS. 16 and 17. Thus, the cutter 1 is detachably incorporated with the tucker 2 by the attraction action of the internally contained magnet 6, permitting the tucker 2 to be rotated on its own axis.

Figure 18:
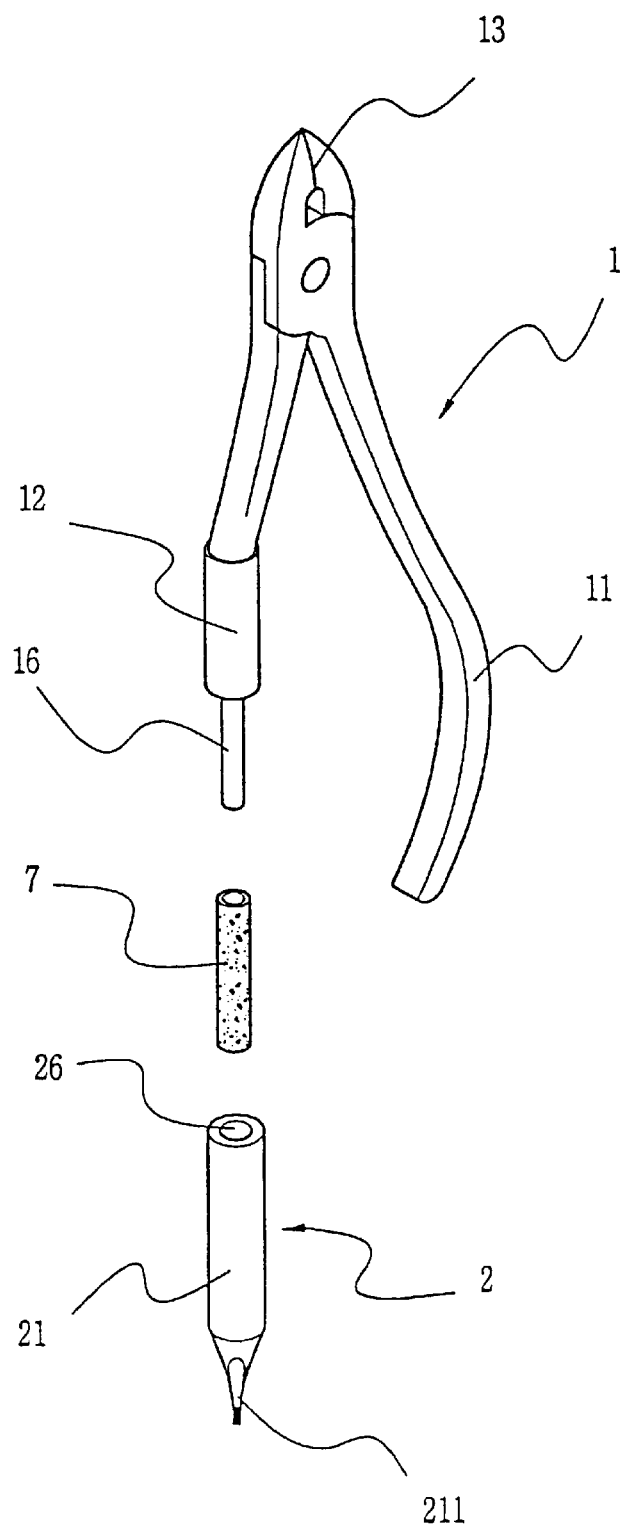
FIG. 18 is a perspective view of an orthodontic cutter in accordance with an eighth embodiment of the present invention.
Figure 19:
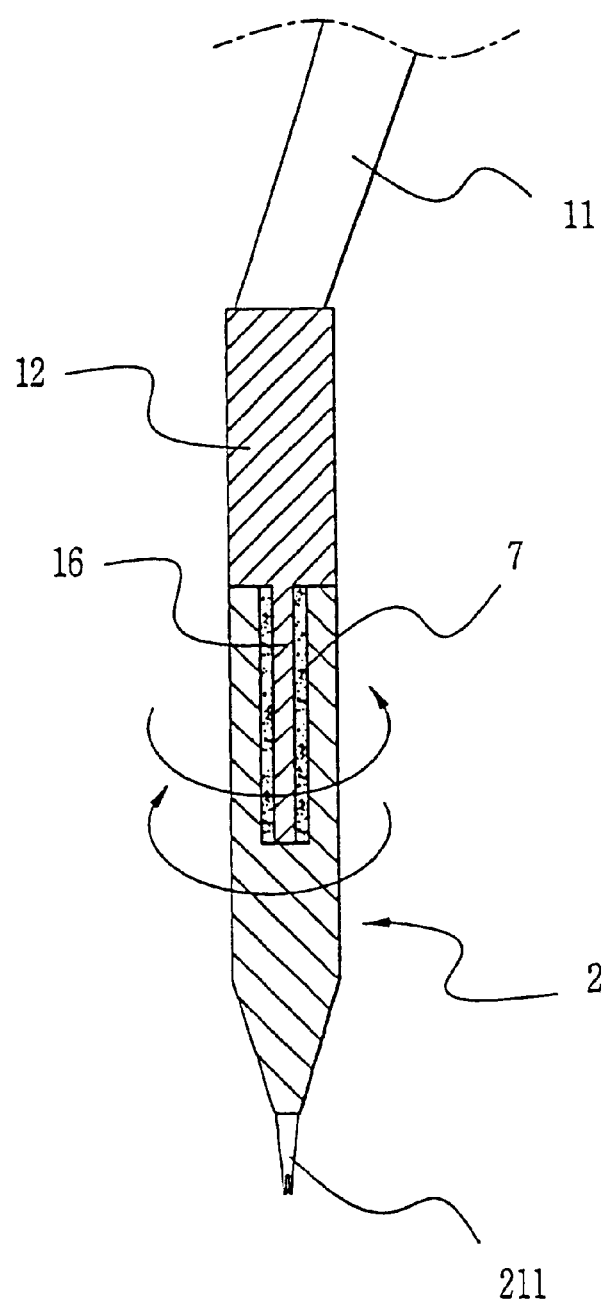
FIG. 19 is a longitudinal sectional view partially illustrating the assembled state of the ligature tucker in accordance with the eighth embodiment of the present invention.

FIG. 18 is an exploded perspective view of an orthodontic cutter in accordance with an eighth embodiment of the present invention, and FIG. 19 is a longitudinal sectional view illustrating the assembled state of the ligature tucker indicated in FIG. 18.

The orthodontic cutter of this embodiment is essentially analogous in structure to that of the first embodiment, excepting that the shorter one of the handles 11 of the cutter 1 is integrally provided with the holder 12 having a stick-type structure without an insertion hole 121 on the lower end thereof, whose lower end is integrally and also centrally provided with a vertically protrusive insertion pole 16 in a desired length, as shown in FIG. 18, and that the tucker 2 has the upper end of the short stick-type handle 21 centrally provided with a magnet pipe-receiving hole 26 having a recessed hollow structure in a desired depth.

Accordingly, when the cutter 1 and the tucker 2 are assembled together, an upright hollow tube-type magnet pipe 7 is inserted into the magnet pipe-receiving hole 26 of the tucker 2 and then the insertion pole 16 of the holder 12 is fitted into the magnet pipe 7, as shown in FIGS. 18 and 19. Thus, the cutter 1 is detachably incorporated with the tucker 2 by the attraction action of the internally contained magnet pipe 7, permitting the tucker 2 to be rotated on its own axis.

Figure 20:
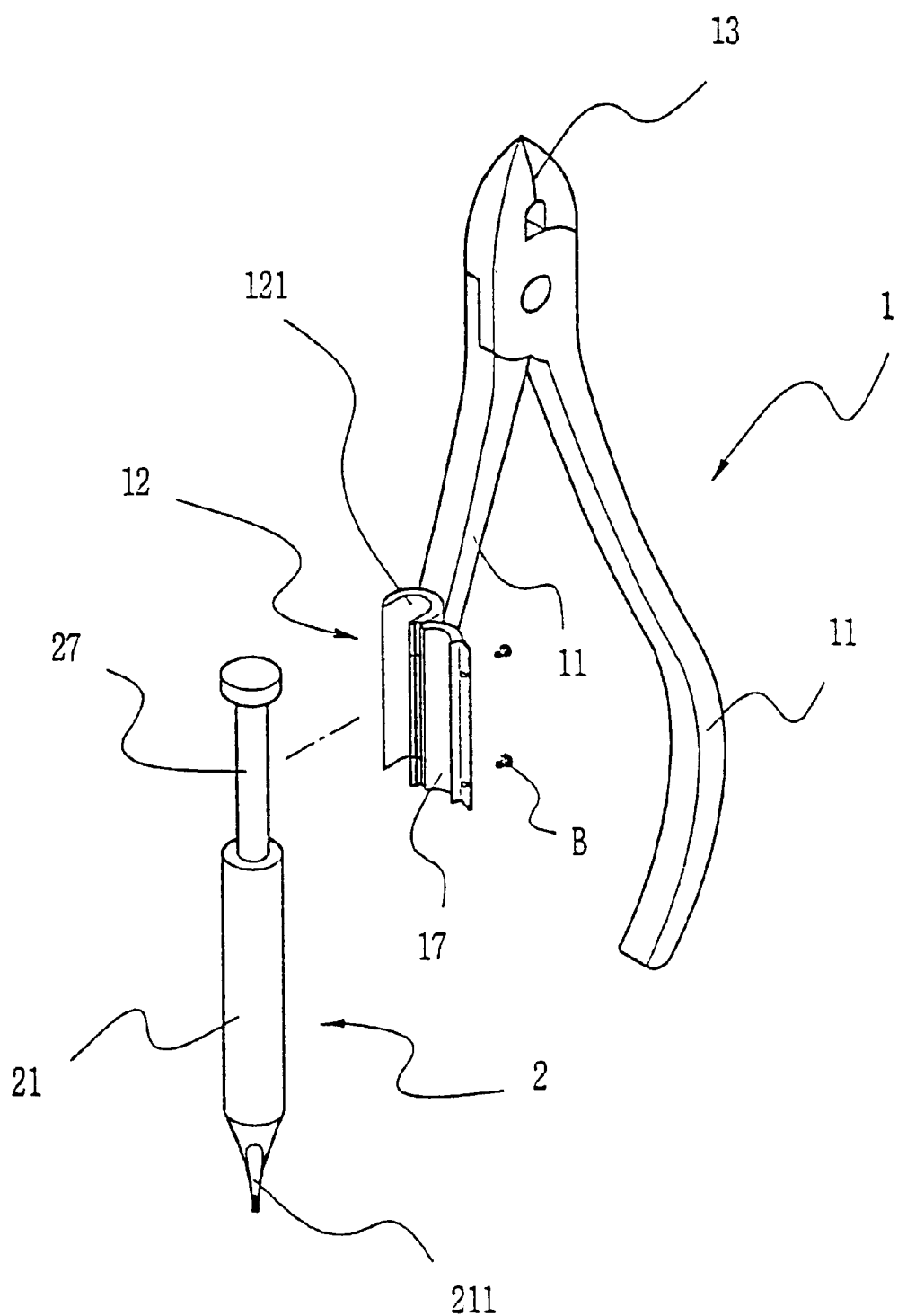
FIG. 20 is a perspective view of an orthodontic cutter in accordance with a ninth embodiment of the present invention.
Figure 21:
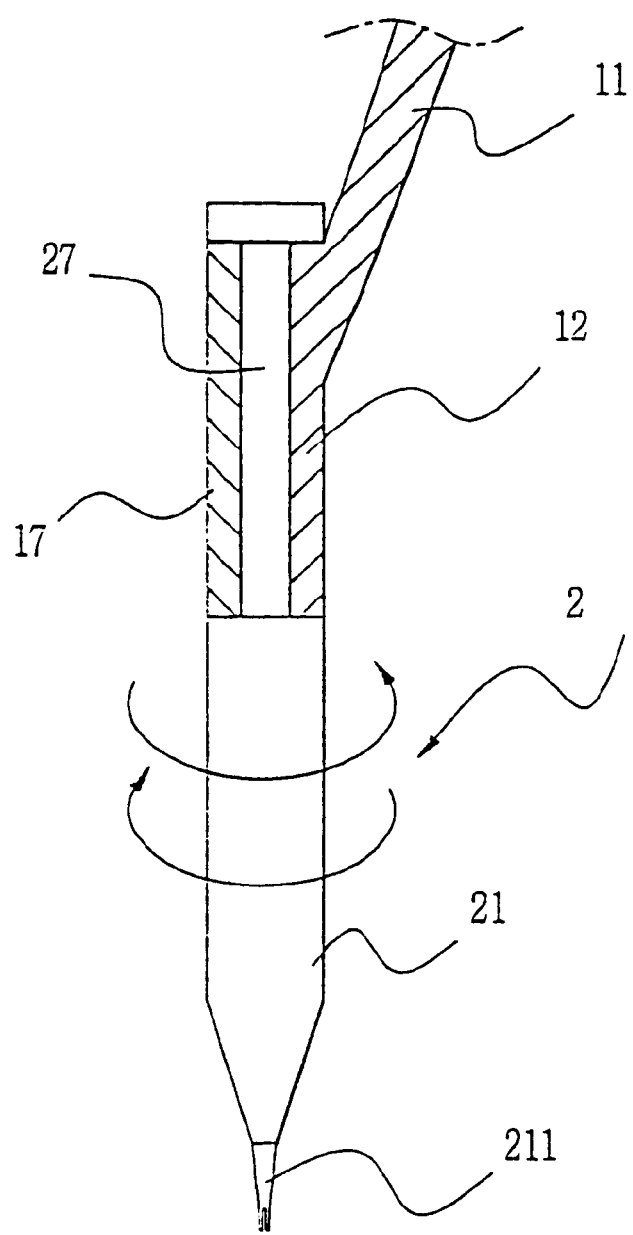
FIG. 21 is a longitudinal sectional view partially illustrating the assembled state of the ligature tucker in accordance with the ninth embodiment of the present invention.

FIG. 20 is an exploded perspective view of an orthodontic cutter in accordance with a ninth embodiment of the present invention, and FIG. 21 is a longitudinal sectional view illustrating the assembled state of the ligature tucker indicated in FIG. 20.

The orthodontic cutter of this embodiment is essentially analogous in structure to that of the first embodiment, excepting that the holder 12 has the lateral side thereof optionally opened by a hinge cap 17 to be secured by two small screw bolts "B" and that the tucker 2 has the upper end of the short stick-type handle 21 integrally provided with a connecting rod 27, as shown in FIG. 20.

The structure of the connecting rod 27 is composed of a vertical portion and a disk, and so takes the shape of "T" if viewed from the front. Said disk is integrally formed on the upper end of said vertical portion and of the same diameter as the outer diameter of the holder 12 and holds said vertical portion in the holder 12.

Accordingly, when the cutter 1 and the tucker 2 are assembled together, said vertical portion of the connecting rod 27 of the tucker 2 is fitted into the insertion hole 121 through the opening created by the opened hinge cap 17, then held in the insertion hole 121 by closing the hinge cap 17, as shown in FIGS. 20 and 21, and then the hinge cap 17 is secured by the two small screw bolts "B". Thus, the cutter 1 is detachably incorporated with the tucker 2.

Said vertical portion of the connecting rod 27 has the diameter slightly less than the width of the opening created by the opened hinge cap 17 and the inner diameter of the insertion hole 121 of the holder 12, and thus the connecting rod 27 is able to pass through the opened hinge cap 17 and to rotate on its axis within the insertion hole 121 of the holder 12.

Figure 22:
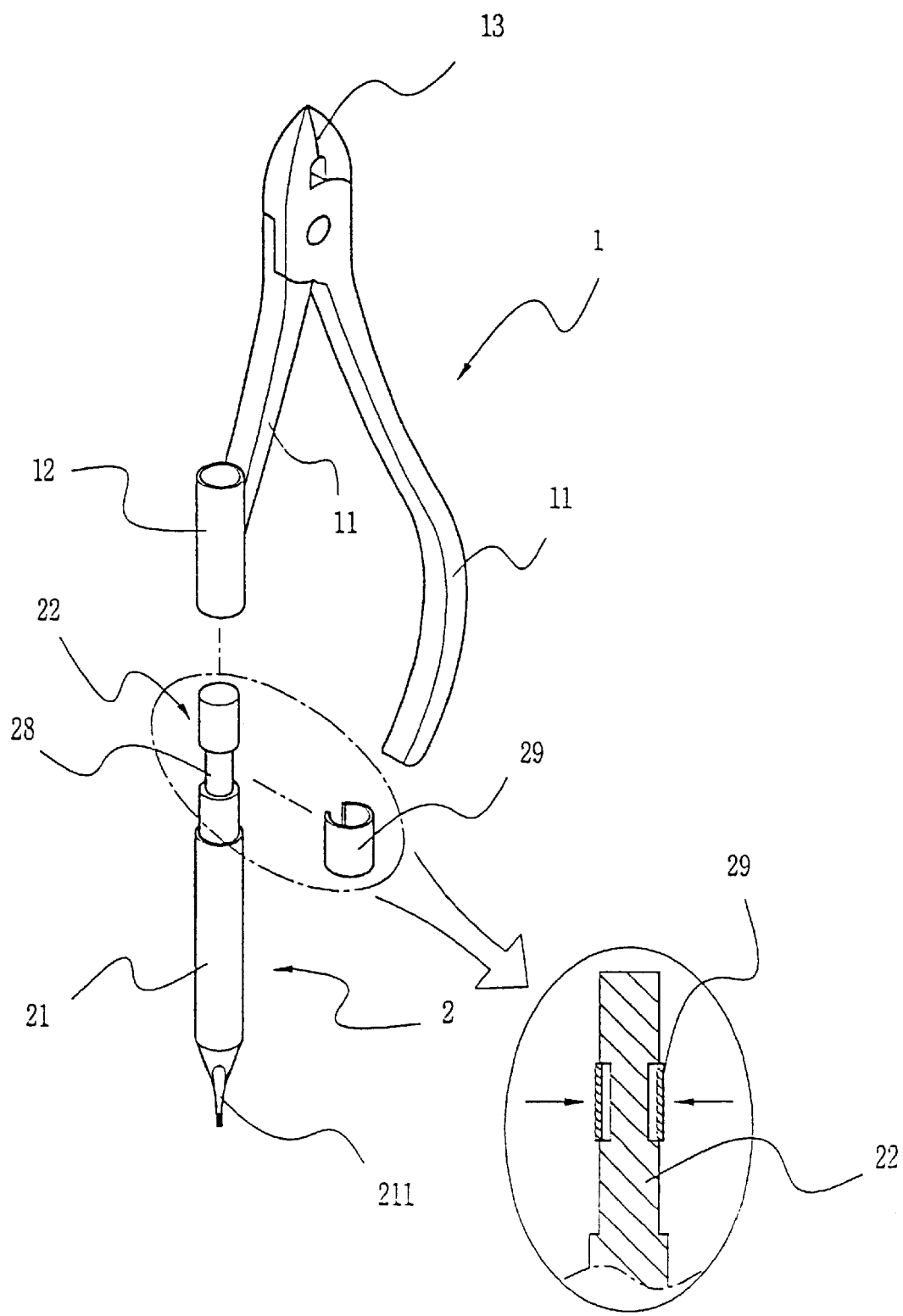
FIG. 22 is a perspective view and partially enlarged longitudinal sectional view of an orthodontic cutter in accordance with a tenth embodiment of the present invention.
Figure 23:
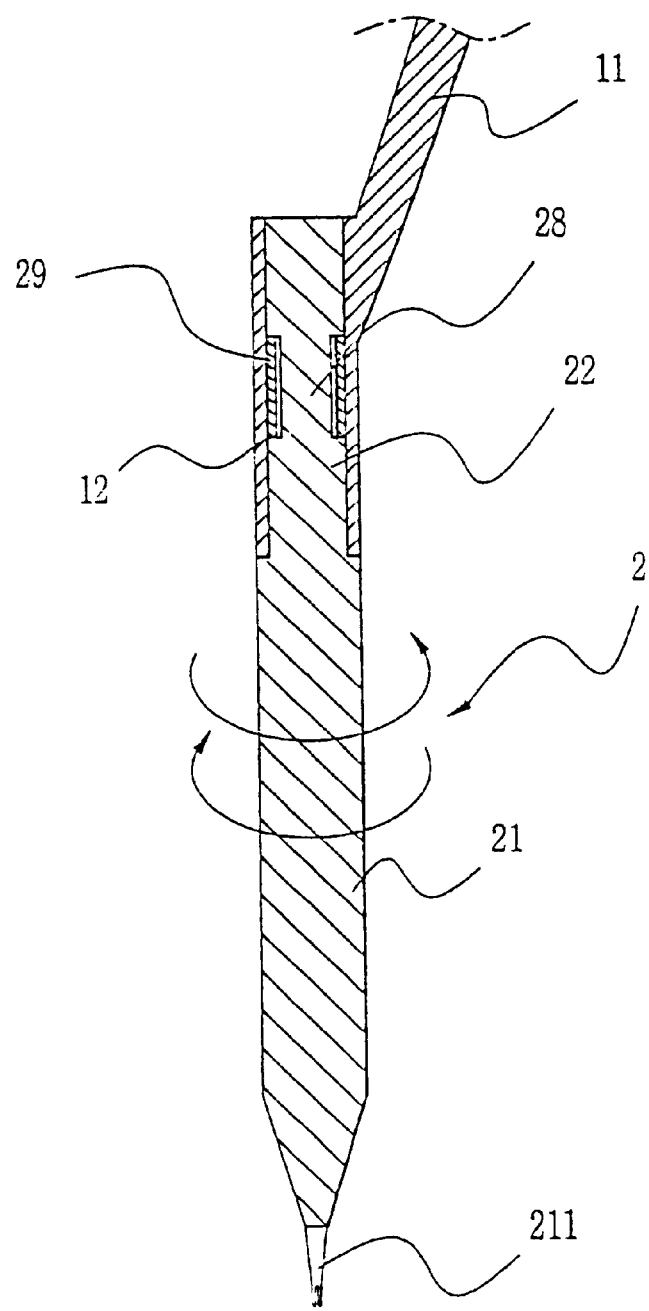
FIG. 23 is a longitudinal sectional view partially illustrating the assembled state of the ligature tucker in accordance with the tenth embodiment of the present invention.

FIG. 22 is an exploded perspective view and partially enlarged longitudinal sectional view of an orthodontic cutter in accordance with a tenth embodiment of the present invention, and FIG. 23 is a longitudinal sectional view illustrating the assembled state of the ligature tucker indicated in FIG. 22.

The orthodontic cutter of this embodiment is essentially analogues in structure to that of the first embodiment, excepting that the insertion post 22 of the tucker 2 has a constricted portion termed a neck 28 and a separate neckband 29 is provide for utilizing a frictional adhesion effect. The neck 28 and the neckband 29 are substitutes for the clamping hole 221 and the clamping bolt 3 of the first embodiment respectively. But, each principle of incorporation is different from the other.

The neck 28 is located in the middle third of the insertion post 22 and has a less diameter than the other portion of the insertion post 22, as shown in FIG. 22.

The neckband 29 is made of a stiff and thin metal plate and has one side completely cutaway in a longitudinal direction, as shown in FIG. 22, to impart the limited flexibility to the side walls thereof as well as to allow itself to be constricted under compressing force. The lateral edges of the cutaway portion of the neckband 29 are spaced apart a somewhat less distance than the diameter of the neck 28 of the insertion post 22 to effect a snap-acting connection to the neck 28 of the insertion post 22. In a passive state, the outer diameter of the neckband 29 is larger than the diameter of the insertion post 22 and the inner diameter of the neckband 29 is larger than the diameter of the neck 28 so as to provide the side walls of the neckband 29 with the space needed to be compressed or constricted but smaller than the diameter of the insertion post 22 so as not to be dislodged after having been engaged with the neck 28, as shown in the partially enlarged longitudinal sectional view of FIG. 22. When the neckband 29 is compressed by finger pressure in the state of engagement with the neck 28 of the insertion post 22, the outer diameter of the neckband 29 changes to a smaller diameter, which permits the neckband 29 to be inserted into the insertion hole 121 of the holder 12 and the inner diameter of the neckband 29 changes to the diameter slightly larger than the diameter of the neck 28, which permits the neck 28 to do a rotation movement on its own axis within the neckband 29, as shown in FIG. 23.

Accordingly, the assembly procedure is as follows. The neckband 29 is initially engaged with the neck 28 of the insertion post 22 with a snap and then firmly compressed by the user's finger pressure to be forcefully inserted into the insertion hole 121. In the state of completed assembly, the sidewalls of the neckband 29 are set to produce a persistent expanding force toward the inner surface of the holder 12 because the neckband 29 has a tendency to spring back to the original form. The expanding force is relatively strong owing to the characteristic of the neckband 29 such as high resistance to the compressing force, and so makes the neckband 29 strongly cling to the internal surface of the holder 12. By virtue of the above-described frictional adhesion action of the internally contained neckband 29, the insertion post 22 can be held in the insertion hole 121. Thus, the cutter 1 is detachably incorporated with the tucker 2, permitting the tucker 2 to be rotated on its own axis.

While not shown in the drawing, there can be provided with the neckband 29 which is shorter than the neck 28 for the sake of allowing the tucker 2 to do the limited up and down movement as well as the rotation movement. The added up and down movement enables the tucking operation to be more accurately done.

It will now be apparent that the orthodontic cutter implemented in accordance with any one of the above-stated embodiments can be effectively used to cut off an excess end of the ligature wire by utilizing the cutter part and then to tuck the sharp end of the ligature wire under the arch wire by utilizing the tucker part incorporated with the cutter part without the necessity of alternately using the separate instruments.

Figure 24:
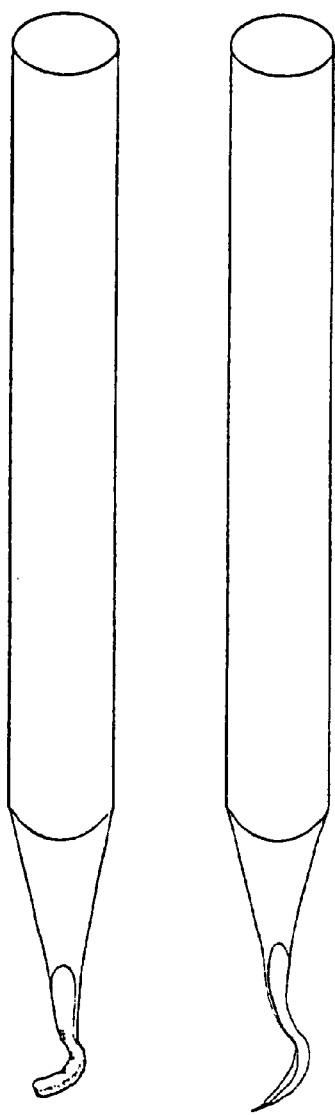
FIG. 24 is a schematic view of a conventional band seater and a conventional scaler.

By way of example, the present invention has been illustrated in terms of an orthodontic cutter incorporated with a ligature tucker in accordance with the first to tenth embodiments, but actually is not limited to the ligature tucker alone. The tucker may be replaceable with any other similar orthodontic hand instrument distinct in configuration of the tip but able to perform the function of the tucker, such as band seater or scaler, by applying the above-described embodiments to a conventional band seater or a conventional scaler illustrated in FIG. 24. The structure of the band seater or scaler consists of a stick-type handle part and a tip part as in the ligature tucker, the tip part assuming the form different from the tip of the ligature tucker. Compared with the tip of the ligature tucker, the tip of the band seater is angled, serrated, wider and thicker, and that of the scaler is sickle-shaped, edged, tapered and larger.

As described above, the novel orthodontic cutter has a single incorporated structure composed of one cutter and one tucker essentially distinct in configuration from each other and of no co-operative relationship, thus eliminating a troublesome step of alternately replacing the separate instruments (cutter and tucker) during an orthodontic treatment work and resultantly providing an enhanced expedience in handling the orthodontic instruments.

On the other hand, the novel orthodontic cutter has a single incorporated structure composed of one cutter and one tucker, allowing the user to optionally detach the cutter or the tucker from the incorporated structure and to easily replace or repair either part upon finding a breakdown of the product, and making it possible to compatibly replace the tucker with any other similar orthodontic hand instrument (e.g., band seater, scaler). Therefore, it can notably meet the user's expectation of the improved orthodontic instrument.

Although several preferred embodiments of the orthodontic cutters of the present invention have been illustrated in the accompanying Drawing and described in the foregoing Detailed Description, it will be understood that the invention is not limited to the embodiments disclosed. Thus, the invention is capable of numerous rearrangements, modifications and substitutions without departing from the sprit of the invention as set forth and defined by the following claims.

What is claimed:

1. An orthodontic cutter, comprising:
   a cutter part including a pair of handles, one of the handles being shorter than the other, which cross at a pivot and a pair of jaws which have cutting edges;
   a tucker part including a short stick-type handle having the lower end thereof provided with a tip;
   a holder formed on the lower lateral side of the shorter one of the handles of the cutter part and provided with an insertion hole;
   an insertion post formed on the top end of the short stick-type handle of the tucker part, provided with a clamping hole in the upper end thereof, and inserted into the insertion hole of the holder; and
   a clamping bolt mated with the clamping hole for holding the insertion post in the insertion hole;
   whereby the tucker part is detachably incorporated with the cutter part, being rotatable on its own axis.

2. The orthodontic cutter of claim 1, wherein said tip of the tucker part assumes the shape of a tip of a band seater.

3. An orthodontic cutter, comprising:
   a cutter part including a pair of handles, one of the handles being shorter than the other, which cross at a pivot and a pair of jaws which have cutting edges;
   a tucker part including a short stick-type handle having the lower end thereof provided with a tip;
   a tapered rod having a desired length, formed on the lower end of the shorter one of the handles of the cutter part, provided with a triangular latch groove around the circumference of the upper portion thereof, and inserted into a socket; and
   the socket having a desired depth, formed in the top end of the short stick-type handle of the tucker part and provided with a pair of vertical slots oppositely positioned from each other in the side walls thereof, a pair of bosses oppositely positioned from each other on the inner and upper surface thereof, and a support pit centrally positioned in the bottom surface thereof, said pair of bosses being engaged with said triangular latch groove, and said support pit being engaged with the lower end of said tapered rod;
   whereby the tucker part is detachably incorporated with the cutter part, being rotatable on its own axis.

4. The orthodontic cutter of claim 3, wherein said tip of the tucker part assumes the shape of a tip of a band seater.

5. An orthodontic cutter, comprising:
   a cutter part including a pair of handles, one of the handles being shorter than the other, which cross at a pivot and a pair of jaws which have cutting edges;
   a tucker part including a short stick-type handle having the lower end thereof provided with a tip;
   a holder formed on the lower lateral side of the shorter one of the handles of the cutter part and provided with an insertion hole;
   a fastening wire; and
   an insertion post formed on the top end of the short stick-type handle of the tucker part, longer than the holder, provided with a fastening hole horizontally piercing the nearly top portion thereof which has passed through the insertion hole of the holder, and held in the holder by said fastening wire inserted into said fastening hole;
   whereby the tucker part is detachably incorporated with the cutter part, being rotatable on its own axis.

6. The orthodontic cutter of claim 5, wherein said tip of the tucker part assumes the shape of a tip of a band seater.

7. An orthodontic cutter, comprising:
   a cutter part including a pair of handles, one of the handles being shorter than the other, which cross at a pivot and a pair of jaws which have cutting edges;
   a tucker part including a short stick-type handle having the lower end thereof provided with a tip;
   a holder formed on the lower end of the shorter one of the handles of the cutter part, including an insertion hole, the upper end of the holder being closed, and provided with a pair of fastening holes horizontally piercing the upper portion thereof;
   a U-shaped fastening wire; and
   an insertion post formed on the top end of the short stick-type handle of the tucker part, provided with a square latch groove prepared around the upper peripheral surface thereof, inserted into the insertion hole of the holder, and held in the holder by said U-shaped fastening wire simultaneously passing through said pair of fastening holes and said square latch groove;
   whereby the tucker part is detachably incorporated with the cutter part, being rotatable on its own axis.

8. The orthodontic cutter of claim 7, wherein said tip of the tucker part assumes the shape of a tip of a band seater.

9. An orthodontic cutter, comprising:
   a cutter part including a pair of handles, one of the handles being shorter than the other, which cross at a pivot and a pair of jaws which have cutting edges;
   a tucker part including a short stick-type handle having the lower end thereof provided with a tip;
   an external screw thread formed on the shorter one of the handles of the cutter part;
   a plunger having a desired length, provided on the lower end of the external screw thread, and inserted into a plunger-receiving hole;
   a flange annularly formed around the periphery of the upper end of the short handle of the tucker part;
   the plunger-receiving hole having a desired depth and centrally provided in the upper end of the short stick-type handle of the tucker part; and
   a coupling nut, a nut stopper and an internal thread of the coupling nut being engaged with the flange and the external screw thread respectively;
   whereby the tucker part is detachably incorporated with the cutter part, being rotatable on its own axis.

10. The orthodontic cutter of claim 9, wherein said tip of the tucker part assumes the shape of a tip of a band seater.

11. An orthodontic cutter, comprising:
    a cutter part including a pair of handles, one of the handles being shorter than the other, which cross at a pivot and a pair of jaws which have cutting edges;
    a tucker part including a short stick-type handle having the lower end thereof provided with a tip;
    a screw bolt;
    an insertion bar formed on the lower end of the shorter one of the handles of the cutter part and provided with a screw hole in the lower end thereof to be mated with said screw bolt;

an interconnection pipe internally provided with an internal thread and a bolt stopper, seated onto the insertion bar, and held in place by said screw bolt mated with said screw hole of the insertion bar; and a screw post formed on the upper end of the short stick-type handle of the tucker part and having an external thread mated with the internal thread of the interconnection pipe;

whereby the tucker part is detachably incorporated with the cutter part, being rotatable on its own axis.

12. The orthodontic cutter of claim 11, wherein said tip of the tucker part assumes the shape of a tip of a band seater.

13. An orthodontic cutter, comprising, a cutter part including a pair of handles, one of the handles being shorter than the other, which cross at a pivot and a pair of jaws which have cutting edges;

a tucker part including a short stick-type handle having the lower end thereof provided with a tip;

a holder formed on the lower end of the shorter one of the handles of the cutter part, provided with an insertion hole, and the upper end of the holder being closed;

a magnet stick-receiving hole having a desired depth and centrally formed in the upper end of the short stick-type handle of the tucker part; and a stick-type magnet, the upper and lower halves of the stick-type magnet being held in the holder and the magnet-stick receiving hole each;

whereby the tucker part is detachably incorporated with the cutter part, being rotatable on its own axis.

14. The orthodontic cutter of claim 13, wherein said tip of the tucker part assumes the shape of a tip of a band seater.

15. An orthodontic cutter, comprising:

a cutter part including a pair of handles, one of the handles being shorter than the other, which cross at a pivot and a pair of jaws which have cutting edges;

a tucker part including a short stick-type handle having the lower end thereof provided with a tip;

a holder formed on the lower end of the shorter one of the handles of the cutter part and including no insertion hole;

an insertion pole formed on the lower end of the holder and having a desired length;

a magnet pipe-receiving hole having a desired depth and centrally formed in the upper end of the short stick-type handle of the tucker part; and a magnet pipe held on the insertion pole as well as held in the magnet pipe-receiving hole;

whereby the tucker part is detachably incorporated with the cutter part, being rotatable on its own axis.

16. The orthodontic cutter of claim 15, wherein said tip of the tucker part assumes the shape of a tip of a band seater.

17. An orthodontic cutter comprising:

a cutter part including a pair of handles, one of the handles being shorter than the other, which cross at a pivot and a pair of jaws which have cutting edges;

a tucker part including a short stick-type handle having the lower end thereof provided with a tip;

a holder formed on the lower lateral side of the shorter one of the handles of the cutter part and including an insertion hole and a hinge cap;

two small screw bolts;

the hinge cap provided at the lateral side of the holder and secured by said two small screw bolts after the insertion of a connecting rod into the insertion hole of the holder; and the connecting rod formed on the upper end of the short stick-type handle of the tucker part and composed of a vertical portion and a disk, said vertical portion of the connecting rod being held in the holder;

whereby the tucker part is detachably incorporated with the cutter part, being rotatable on its own axis.

18. The orthodontic cutter of claim 17, wherein said tip of the tucker part assumes the shape of a tip of a band seater.

19. An orthodontic cutter comprising:

a cutter part including a pair of handles, one of the handles being shorter than the other, which cross at a pivot and a pair of jaws which have cutting edges;

a tucker part including a short stick-type handle having the lower end thereof provided with a tip;

a holder formed on the lower lateral side of the shorter one of the handles of the cutter part and provided with an insertion hole;

an insertion post having a neck in the middle third thereof, formed on the upper end of the short stick-type handle of the tucker part and inserted into the insertion hole of the holder; and a neckband having one side completely cutaway in a longitudinal direction, engaged with the neck of the insertion post and held in the insertion hole of the holder in a compressed state;

whereby the tucker part is detachably incorporated with the cutter part, being rotatable on its own axis.

20. The orthodontic cutter of claim 19, wherein said tip of the tucker part assumes the shape of a tip of a band seater.

* * * * *